(12) United States Patent
Itier et al.

(10) Patent No.: US 8,852,878 B2
(45) Date of Patent: Oct. 7, 2014

US008852878B2

(54) METHOD FOR IDENTIFYING AN ANTAGONIST OF GUANINE NUCLEOTIDE RELEASING FACTOR 1

(75) Inventors: Jean-Michel Itier, Savigny sur Orge (FR); Marie-Christine Multon, Versailles (FR); Gwénaëlle Ret, Naisons-Alfort (FR); Jean-Marie Stutzmann, Villecresnes (FR); Florence Wahl, Boulogne (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 13/197,242

(22) Filed: Aug. 3, 2011

(65) Prior Publication Data

US 2012/0009604 A1    Jan. 12, 2012

Related U.S. Application Data

(63) Continuation of application No. 10/344,223, filed as application No. PCT/FR01/02561 on Aug. 7, 2001, now abandoned.

(30) Foreign Application Priority Data

Aug. 10, 2000 (FR) .................................... 00 10539

(51) Int. Cl.
*G01N 33/53* (2006.01)
*G01N 33/567* (2006.01)
*G01N 33/68* (2006.01)

(52) U.S. Cl.
CPC .... *G01N 33/6893* (2013.01); *G01N 2333/4703* (2013.01); *G01N 33/6896* (2013.01); *G01N 2500/04* (2013.01); *G01N 2500/10* (2013.01); *G01N 33/6872* (2013.01)
USPC .......................................... 435/7.92; 435/29

(58) Field of Classification Search
CPC .......... G01N 33/6872; G01N 33/6893; G01N 33/6896; G01N 2500/10
USPC .................................................. 435/7.92, 29
See application file for complete search history.

(56) References Cited

U.S. PATENT DOCUMENTS

| | | | | |
|---|---|---|---|---|
| 5,426,029 | A * | 6/1995 | Rittershaus et al. | 435/7.21 |
| 5,518,911 | A * | 5/1996 | Abo et al. | 435/194 |
| 5,656,595 | A | 8/1997 | Schweighoffer et al. | |
| 6,037,463 | A * | 3/2000 | Uhlmann et al. | 536/24.5 |
| 6,238,881 | B1 * | 5/2001 | Hart | 435/69.1 |
| 6,340,575 | B1 * | 1/2002 | Bollag et al. | 435/69.1 |
| 6,589,773 | B1 * | 7/2003 | Khazak | 435/254.21 |

FOREIGN PATENT DOCUMENTS

| | | |
|---|---|---|
| WO | PCT/FR93/00382 | 4/1993 |
| WO | PCT/CA00/00042 | 1/2000 |
| WO | PCT/EP00/00042 | 1/2000 |

OTHER PUBLICATIONS

Bolon, 2004, Basic & Clinical Pharmacology & Toxicology, vol. 95, pp. 154-161.*
Fernandez-Metarde, 2011, Biochimica et Biophysica Acta, vol. 1815, pp. 170-188.*
Vickers, 2012, Neuropharmacology, vol. 63, pp. 124-131.*
Huang, 1990, PNAS, vol. 87, pp. 8008-8012.*
Itier, 1998, Nature, vol. 393, pp. 125-126.*
Kiyono, 1999, PNAS, vol. 96, pp. 4826-4831.*
Mattingly, 1996, Nature, vol. 382, Issue Jul. 18, pp. 268-272.*
Gross, 1999, Biochemistry, vol. 38, vol. 38, pp. 13252-13262.*
Cen, 1992, EMBO Journal, vol. 11, issue 11, pp. 4007-4015.*
Gould, 1998, Genetics, vol. 149, pp. 1221-1233.*
Tu, 1999, Molecular and Cellular Biology, vol. 19, issue 1, pp. 602-611.*
Stang, 1997, Molecular and Cellular Biology, vol. 17, Issue 6, pp. 3047-3055.*
Mosteller, 1995, methods of Enzymology, vol. 255, pp. 135-148.*
Masuda, 2000, Journal of Virology, vol. 74, Issue 6, pp. 2636-2646.*
Yamakawa, 1994, Osaka City Medical Journal, vol. 40, No. 2, pp. 71-81.*
Martegani, 1992, the EMOB Journal, vol. 11, issue 6, pp. 2151-2157.*
Russell, 1986, Cell, vol. 45, pp. 145-153.*
Chevallier-Multon, 1993, the Journal of Biological Chemistry, vol. 288, No. 15, pp. 11113-11118.*
Bagrodia Shubha et al., PAK to The Future, Trends in Cell Biology, (1999), vol. 9, pp. 350-355.
Barash Ilona A. et al., Leptin is a Metabolic Signal to the Reproductive System, Endocrinology, (1996), vol. 137, No. 7, pp. 3144-3147.
Barlat I. et al., The Saccharomyces Cerevisiae Gene Product SDC25 C-Domain Functions as an Oncoprotein in NIH3T3 Cells, Oncogene, (1993), vol. 8, pp. 215-218.
Bederson Joshua B. et al., Rat Middle Cerebral Artery Occlusion: Evaluation of The Model and Development of a Neurologic Examination, Stroke, (1986), vol. 17, No. 3, pp. 472-476.
Bekre S. et al., Detailed Map of a Region Commonly Amplified at 11q13 q14 in Human Breast Carcinoma, Cytogenet Cell Genet, (1997), vol. 79, pp. 125-131.
Bonner Tom I. et al., The Complete Coding Sequence of the Human raf Ocogene and the Corresponding Structure of the c-raf-1 Gene, Nucleic Acids Research, (1986), Vol, 14, No. 2, pp. 1009-1015.
Bouloumie Anne et al., Leptin, The Product of Ob Gene, Promotes Angiogenesis, Circulation Research, (1998), vol. 83, pp. 1059-1066.
Brambilla Riccardo et al., A Role for the Ras Signalling Pathway in Synaptic Transmission and Long-Term memory, Nature, (1997), vol. 390, pp. 281-286.

(Continued)

*Primary Examiner* — Prema Mertz
(74) *Attorney, Agent, or Firm* — Lathrop & Gage LLP; James H. Velema, Esq.

(57) ABSTRACT

The invention concerns the use of whole or part of the GRF1 protein, or of cells expressing whole or part of the GRF1 protein, in methods for detecting compounds for preventing and/or treating pathologies or disorders of the central nervous system involving neuronal death, such as apoptosis, or related to leptin metabolism. The pathologies of the central nervous system are in particular cerebral ischemia, Parkinson's disease or Alzheimer's disease.

12 Claims, 6 Drawing Sheets

(56) References Cited

OTHER PUBLICATIONS

Figure 1A:
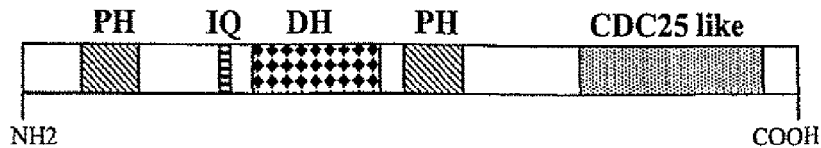

Brown Jeffrey L. et al., Human Ste20 Homologue hPAK1 Links GTPases to the JNK MAP Kinase Pathway, Current Biology, (1996), vol. 6, No. 5, pp. 598-605.

Capon Daniel J. et al., Complete Nucleotide Sequences of the T24 Human Bladder Carcinoma Oncogene and its Normal Homologue, Nature, (1983), vol. 302, pp. 33-37.

Chatton Bruno et al., Eukaryotic GST Fusion Vector for the Study of Protein-Protein Associations In Vivo: Application to Interaction of ATFa With June and Fos, BioTechniques, (1995), vol. 18, No. 1.

Chehab Farid F. et al., Correction of the Sterility Defect in Homozygous Obese Female Mice by Treatment With the Human Recombinant Leptin, Nature Genetics, (1996), vol. 12, pp. 318-320.

Chehab Farid F. et al., Early Onset of Reproductive Function in Normal Female Mice Treated With Leptin, Science, (1997), vol. 275, pp. 88-90.

Clement Karine et al., A Mutation in the Human Leptin Receptor Gene Causes Obesity and Pituitary Dysfunction, Nature, (1998), vol. 392, pp. 398-401.

Drivas George T. et al., Characterization of Four Novel ras-Like Genes Expressed in a Human Teratocarcinoma Cell Line, Molecular and Cellular Biology, (1990), vol. 10, No. 4, pp. 1793-1798.

Ducy Patricia et al., Leptin Inhibits Bone Formation Through a Hypothalamic Relay: A Central Control of Bone Mass, Cell, (2000), vol. 100, pp. 197-207.

Emerson S. Donald et al., Solution Structure of the Ras-Binding Domain of c-Raf-1 and Identification of Its Ras Interaction Surface, Biochemistry, (1995), vol. 34, No. 21, pp. 6911-6918.

Farnsworth Charles L. et al., Calcium Activation of Ras Mediated by Neuronal Exchange Factor Ras-Grf, Nature, (1995), vol. 376, pp. 524-527.

Freshney Norman W. et al., Activation of the Exchange Factor Ras-GRF by Calcium Requires an Intact Dbl Homology Domain, FEBS Letters, (1997), pp. 111-115.

Friedman Jeffrey M. et al., Leptin and the Regulation of Body Weight in Mammals, Nature, (1998), vol. 395, pp. 763-770.

Gietz R. Daniel et al., Studies on the Transformation of Intact Yeast Cells by the LiAc/SS-DNA/PEG Procedure, Yeast, (1995), vol. 11, pp. 355-360.

Hall Alan, Rho GTPases and the Actin Cytosckeleton, Science, (1998), vol. 279, pp. 509-514.

Han Jaewon et al., Lck Regulates Vav Activation of Members of the Rho Family of GTPases, Mollecular and Cellular Biology, (1997), vol. 17, No. 3, pp. 1346-1353.

Kamada Shinji et al., A Cloning Method for Caspase Substrates That Uses the Yeast Two-Hybrid System: Cloning of the Antiapoptotic Gene Gelsolin, Proceedings of the National Academy Sciences of the United States of America, (1998), vol. 95, pp. 8532-8537.

Kiyono Mari et al., G Protein Beta Gamma Subunit-Dependent Rac-Guanine Nucleotide Exchange Activity of Ras-GRF1/CDC25Mm, Proceedings of the National Academy Sciences of The United States of America, (1999), vol. 96, pp. 4826-4831.

Kristensen Peter et al., Hypothalamic CART is a New Anorectic Peptide Regulated by Leptin, Nature, (1998), vol. 393, pp. 72-76.

Krude Heiko et al., Severy Early-Onse Obesity, Adrenal Insufficiency and Red Hair Pigmentation Caused by POMC Mutations in Humans, Nature Genetics, (1998), vol. 19, pp. 155-158.

Leanna Candice A. et al., The Reverse Two-Hybrid System: A Genetic Scheme for Selection Against Specific Protein/Protein Interactions, Nucleic Acids Research, (1996), vol. 24, No. 17, pp. 3341-3347.

Lord Graham M. et al., Leptin Modulates the T-Cell Immune Response and Reverses Starvation-Induced Immunosuppression, Nature, (1998), vol. 394, pp. 897-901.

Martegani Enzo et al., Cloning by Functional Complementation of a Mouse cDNA Encoding a Homologue, of CDC25, A Saccharomyces Cerevisiae RAS Activator, The EMBO Journal, (1992), vol. 11, No. 6, pp. 2151-2157.

Mattingly Raymond et al., Phosphorylation-Dependent Activation of the Ras-GRF/CDC25Mm Exchange Factor by Muscarinic Receptors and G-Protein Beta Gamma Subunits, Nature, (1996), vol. 382, pp. 268-272.

Mosteller Raymond D. et al., Analysis of Interaction Between Ras and CDC25 Guanine Nucleotide Exchange Factor Using Yeast GAL4 Two-Hybrid System, Methods in Enzymology, (1995), vol. 255, pp. 135-148.

Mott Helen R. et al., The Solution Structure of the Raf-1 Cysteine-Rich Domain: A Novel Ras and Phospholipid Binding Site, Proc. Nat'l. Acad. Sci. USA, (1996), vol. 93, pp. 8312-8317.

McGrath John P. et al., Structure and Organization of the Human Ki-ras proto-oncogene and a Related Processed Pseudogene, Nature, (1983), vol. 304, pp. 501-506.

Nassar Nicolas et al., Ras/Rap Effector Specificity Determined by Charge Reversal, Nature Structural Biology, (1996), vol. 3, No. 7, pp. 723-729.

Nassar Nicolas et al., The 2.2A Crystal Structure of the Ras-Binding Domain of the Serine/Threonine Kinase c-Raf1 in Complex With Rap1A and a GTP Analogue, Nature, (1995), vol. 375, pp. 554-560.

Plass Christoph et al., Identification of Grf1 on Mouse Chromosome 9 as an Imprinted Gene by RLGS-M, Nature Genetics, (1996), vol. 14, pp. 106-109.

Polakis Paul G. et al., Identification of the ral and rac1 Gene Products, Low Molecular Mass GTP-Binding Proteins From Human Platelets, The Journal of Biological Chemistry, (1969), vol. 254, No. 28, pp. 16383-16389.

Sanders Luraynne C. et al., Inhibition of Myosin Light Chain Kinase by p21-Activated Kinase, Science, (1999), vol. 283, pp. 2083-2085.

Sawai Tohru et al., Interaction Between Pleckstrin Homology Domains and G Protein Beta Gamma Subunits: Analyses of Kinetic Parameters by a Biosensor-Based Method, Biological & Pharmaceutical Bulletin, (1999), vol. 22, No. 3, pp. 229-233.

Schwartz Michael W. et al., Indentification of Targets of Leptin Action in Rat Hypotalamus, Journal of Clinical Investigation, (1996), vol. 98, No. 5, pp. 1101-1106.

Schweighoffer Fabien et al., Identification of a Human Guanine Nucleotide-Releasing Factor (H-GRF55) Specific for Ras Proteins, Oncogene, (1993), vol. 8, pp. 1477-1485.

Shinjo Katsuhiro et al., Molecular Cloning of the Gene for the Human Placental GTP-Binding Protein Gp (G25K): Identificaition of This GTP-Binding Protein as the Human Homolog of the Yeast Cell-Division-Cycle Protein CDC42, Proc. Nat'l. Acad. Sci. USA, (1990), vol. 87, pp. 9853-9857.

Shou Chengchao et al., Differential Response of the Ras Exchange Factor, Ras-GRF to Tyrosine Kinase and G Protein Mediated Signals, Oncogene, (1995), vol. 10, pp. 1887-1893.

Shou Chengchao et al., Molecular Cloning of cDNAs Encoding a Guanine-Nucleotide-Releasing Factor for Ras p21, Nature, (1992), vol. 358, pp. 351-354.

Sierra-Honigmann M. Rocio et al., Biological Action of Leptin as an Angiogenic Factor, Science, (1998), vol. 281, pp. 1683-1686.

Strobel Andreas et al., A Leptin Missense Mutation Associated With Hypogonadism and Morbid Obesity, Nature Genetics, (1998), vol. 18, pp. 213-215.

Tamura A. et al., Focal Cerebral Ischaemia in the Rat: 1. Description of Technique and Early Neuropathological Consequences Following Middle Cerebral Artery Occlusion, Journal of Cerebral Blood Flow and Metabolism, (1981), vol. 1, No. 1, pp. 53-60.

Taparowsky Elizabeth et al., Structure and Activation of the Human N-Ras Gene, Cell, (1983), vol. 34, pp. 581-586.

Thiele Todd E et al., Ethanol Consumption and Resistance Are Inversely Related to Neuropeptide Y Levels, Nature, (1998), vol. 396, pp. 366-369.

Thompson Gladstone et al., Delineation of the Cdc42/Rac-Binding Domain of p21-Activated Kinase, Biochemistry, (1998), vol. 37, pp. 7885-7891.

Touhara Kasushige et al., Binding of G Protein Beta Gamma Subunits to Pleckstrin Homology Domains, The Journal of Biological Chemistry, (1994), vol. 280, No. 14, pp. 10217-10220.

Vojtek Anne B. et al., Mammalian Ras Iriteracts Directly With the Serine/Threonine Kinase Raf, Cell, (1993), vol. 74, pp. 205-214.

(56) References Cited

OTHER PUBLICATIONS

Wei Wen et al., Localization of the Cellular Expression Pattern of cdc25nef and ras in the Juvenile Rat Brain, Molecular Brain Research, (1993), vol. 19, pp. 339-344.

Zippel Reneta et al., The Brain Specific Ras Exchange Factor CDC25Mm: Modulation of Its Activity Through Gi-Protein-Mediated Signals, Oncogene, (1996), vol. 12, pp. 2697-2703.

A Frameshift Mutation in Human MC4R Is Associated With a Dominant Form of Obesity, Nature Genetics.

Imprinted Gene in Postnatal Growth Role, Nature, (1998), vol. 393, pp. 125-126.

Zee et al., "Dual Specificity of the Interfacial Inhibitor Brefeldin A for Art Proteins and Sec7 Domains", J. Biological Chemistry, vol. 281, No. 17, pp. 11805-11814 (Apr. 28, 2006) (Exhibit A).

Fasano et al., "Inhibition of Ras-guanine nucleotide—releasing factor 1 (Ras-GRF1) signaling in the striatum reverts motor symptoms associated with L-dopa-induced dyskinesia", PNAS, vol. 107, No. 50 (Dec. 14, 2010) (Exhibit B).

* cited by examiner

SEQUENCE LISTING

```
<160> NUMBER OF SEQ ID NOS: 3

<210> SEQ ID NO 1
<211> LENGTH: 1275
<212> TYPE: PRT
<213> ORGANISM: Homo sapiens
```

<400> SEQUENCE: 1

```
Met Gln Lys Ala Ile Arg Leu Asn Asp Gly His Val Ala Pro Leu Gly
  1               5                  10                  15

Leu Leu Ala Arg Lys Asp Gly Thr Arg Lys Gly Tyr Leu Ser Lys Arg
             20                  25                  30

Ser Ser Asp Asn Thr Lys Trp Gln Thr Lys Trp Phe Ala Leu Leu Gln
         35                  40                  45

Asn Leu Leu Phe Tyr Phe Glu Ser Asp Ser Ser Arg Pro Ser Gly
     50                  55                  60

Leu Tyr Leu Leu Glu Gly Cys Val Cys Asp Arg Ala Pro Ser Pro Lys
 65                  70                  75                  80

Pro Ala Leu Ser Ala Lys Glu Pro Leu Glu Lys Gln His Tyr Phe Thr
                 85                  90                  95

Val Asn Phe Ser His Glu Asn Gln Lys Ala Leu Glu Leu Arg Thr Glu
                100                 105                 110

Asp Ala Lys Asp Cys Asp Glu Trp Val Ala Ala Ile Ala His Ala Ser
                115                 120                 125

Tyr Arg Thr Leu Ala Thr Glu His Glu Ala Leu Met Gln Lys Tyr Leu
        130                 135                 140

His Leu Leu Gln Ile Val Glu Thr Glu Lys Thr Val Ala Lys Gln Leu
145                 150                 155                 160

Arg Gln Gln Ile Glu Asp Gly Glu Ile Glu Ile Glu Arg Leu Lys Ala
                    165                 170                 175

Glu Ile Thr Ser Leu Leu Lys Asp Asn Glu Arg Ile Gln Ser Thr Gln
                180                 185                 190

Thr Val Ala Pro Asn Asp Glu Asp Ser Asp Ile Lys Lys Ile Lys Lys
            195                 200                 205

Val Gln Ser Phe Leu Arg Gly Trp Leu Cys Arg Arg Lys Trp Lys Thr
    210                 215                 220

Ile Ile Gln Asp Tyr Ile Arg Ser Pro His Ala Asp Ser Met Arg Lys
225                 230                 235                 240

Arg Asn Gln Val Val Phe Ser Met Leu Glu Ala Glu Ala Glu Tyr Val
                245                 250                 255

Gln Gln Leu His Ile Leu Val Asn Asn Phe Leu Arg Pro Leu Arg Met
            260                 265                 270

Ala Ala Ser Ser Lys Lys Pro Pro Ile Thr His Asp Asp Val Ser Ser
        275                 280                 285

Ile Phe Leu Asn Ser Glu Thr Ile Met Phe Leu His Gln Ile Phe Tyr
    290                 295                 300

Gln Gly Leu Lys Ala Arg Ile Ser Ser Trp Pro Thr Leu Val Leu Ala
305                 310                 315                 320

Asp Leu Leu Asp Ile Leu Leu Pro Met Leu Asn Ile Tyr Gln Glu Phe
                325                 330                 335

Val Arg Asn His Gln Tyr Ser Leu Gln Ile Leu Ala His Cys Lys Gln
            340                 345                 350

Asn Arg Asp Phe Asp Lys Leu Leu Lys His Tyr Glu Ala Lys Pro Asp
        355                 360                 365

Cys Glu Glu Arg Thr Leu Glu Thr Phe Leu Thr Tyr Pro Met Phe Gln
    370                 375                 380

Ile Pro Arg Tyr Ile Leu Thr Leu His Asp Val Leu Ala His Thr Pro
385                 390                 395                 400

His Glu His Val Glu Arg Asn Ser Leu Asp Tyr Ala Lys Ser Lys Leu
```

```
            405                 410                 415
Glu Glu Leu Ser Arg Ile Met His Asp Glu Val Ser Glu Thr Glu Asn
            420                 425                 430

Ile Arg Lys Asn Leu Ala Ile Glu Arg Met Ile Ile Glu Gly Cys Glu
            435                 440                 445

Ile Leu Leu Asp Thr Ser Gln Thr Phe Val Arg Gln Gly Ser Leu Ile
            450                 455                 460

Gln Val Pro Met Ser Glu Lys Gly Lys Ile Thr Arg Gly Arg Leu Gly
465                 470                 475                 480

Ser Leu Ser Leu Glu Lys Glu Gly Arg Gln Cys Phe Leu Phe Ser
            485                 490                 495

Lys His Leu Ile Ile Cys Thr Arg Gly Ser Gly Lys Leu His Leu
            500                 505                 510

Thr Lys Asn Gly Val Ile Ser Leu Ile Asp Cys Thr Leu Leu Glu Glu
            515                 520                 525

Pro Glu Ser Thr Glu Glu Ala Lys Gly Ser Gly Gln Asp Ile Asp
530                 535                 540

His Leu Asp Phe Lys Ile Gly Val Glu Pro Lys Asp Ser Pro Phe
545                 550                 555                 560

Thr Val Ile Leu Val Ala Ser Ser Arg Gln Glu Lys Ala Ala Trp Thr
            565                 570                 575

Ser Asp Ile Ser Gln Cys Val Asp Asn Ile Arg Cys Asn Gly Leu Met
            580                 585                 590

Met Asn Ala Phe Glu Glu Asn Ser Lys Val Thr Val Pro Gln Met Ile
            595                 600                 605

Lys Arg Thr Arg Glu Gly Thr Arg Glu Ala Glu Met Ser Arg Ser Asp
            610                 615                 620

Ala Ser Leu Tyr Cys Asp Asp Val Asp Ile Arg Phe Ser Lys Thr Met
625                 630                 635                 640

Asn Ser Cys Lys Val Leu Gln Ile Arg Tyr Ala Ser Val Glu Arg Leu
            645                 650                 655

Leu Glu Arg Leu Thr Asp Leu Arg Phe Leu Ser Ile Asp Phe Leu Asn
            660                 665                 670

Thr Phe Leu His Ser Tyr Arg Val Phe Thr Thr Ala Ile Val Val Leu
            675                 680                 685

Asp Lys Leu Ile Thr Ile Tyr Lys Lys Pro Ile Ser Ala Ile Pro Ala
690                 695                 700

Arg Trp Leu Arg Ser Leu Glu Leu Leu Phe Ala Ser Gly Gln Asn Asn
705                 710                 715                 720

Lys Leu Leu Tyr Gly Glu Pro Pro Lys Ser Pro Arg Ala Thr Arg Lys
            725                 730                 735

Phe Ser Ser Pro Pro Leu Ser Ile Thr Lys Thr Ser Ser Pro Ser
            740                 745                 750

Arg Arg Arg Lys Leu Ile Ser Leu Asn Ile Pro Ile Ile Thr Gly Gly
            755                 760                 765

Lys Ala Leu Asp Leu Ala Gly Ser Leu Ser Cys Asn Ser Asn Gly Tyr
            770                 775                 780

Thr Ser Met Tyr Ser Ala Met Ser Pro Phe Ser Lys Ala Thr Leu Asp
785                 790                 795                 800

Thr Ser Lys Leu Tyr Val Ser Ser Phe Thr Asn Lys Ile Pro Asp
            805                 810                 815

Glu Gly Asp Thr Thr Pro Glu Lys Pro Glu Asp Pro Ser Ala Leu Ser
            820                 825                 830
```

Lys Gln Ser Ser Glu Val Ser Met Arg Glu Ser Asp Ile Asp Gln
            835                 840                 845

Asn Gln Ser Asp Asp Gly Asp Thr Glu Thr Ser Pro Thr Lys Ser Pro
850                 855                 860

Thr Thr Pro Lys Ser Val Lys Asn Lys Asn Ser Ser Glu Phe Pro Leu
865                 870                 875                 880

Phe Ser Tyr Asn Asn Gly Val Val Met Thr Ser Cys Arg Glu Leu Asp
            885                 890                 895

Asn Asn Arg Ser Ala Leu Ser Ala Ala Ser Ala Phe Ala Ile Ala Thr
            900                 905                 910

Ala Gly Ala Asn Glu Gly Thr Pro Asn Lys Glu Lys Tyr Arg Arg Met
            915                 920                 925

Ser Leu Ala Ser Ala Gly Phe Pro Pro Asp Gln Arg Asn Gly Asp Lys
            930                 935                 940

Glu Phe Val Ile Arg Arg Ala Ala Thr Asn Arg Val Leu Asn Val Leu
945                 950                 955                 960

Arg His Trp Val Ser Lys His Ser Gln Asp Phe Glu Thr Asn Asp Glu
                965                 970                 975

Leu Lys Cys Lys Val Ile Gly Phe Leu Glu Glu Val Met His Asp Pro
            980                 985                 990

Glu Leu Leu Thr Gln Glu Arg Lys Ala Ala Ala Asn Ile Ile Arg Thr
            995                 1000                1005

Leu Thr Gln Glu Asp Pro Gly Asp Asn Gln Ile Thr Leu Glu Glu Ile
    1010                1015                1020

Thr Gln Met Ala Glu Gly Val Lys Ala Glu Pro Phe Glu Asn His Ser
1025                1030                1035                1040

Ala Leu Glu Ile Ala Glu Gln Leu Thr Leu Leu Asp His Leu Val Phe
                1045                1050                1055

Lys Lys Ile Pro Tyr Glu Glu Phe Phe Gly Gln Gly Trp Met Lys Leu
            1060                1065                1070

Glu Lys Asn Glu Arg Thr Pro Tyr Ile Met Lys Thr Thr Lys His Phe
            1075                1080                1085

Asn Asp Ile Ser Asn Leu Ile Ala Ser Glu Ile Ile Arg Asn Glu Asp
            1090                1095                1100

Ile Asn Ala Arg Val Ser Ala Ile Glu Lys Trp Val Ala Val Ala Asp
1105                1110                1115                1120

Ile Cys Arg Cys Leu His Asn Tyr Asn Ala Val Leu Glu Ile Thr Ser
                1125                1130                1135

Ser Met Asn Arg Ser Ala Ile Phe Arg Leu Lys Lys Thr Trp Leu Lys
            1140                1145                1150

Val Ser Lys Gln Thr Lys Ala Leu Ile Asp Lys Leu Gln Lys Leu Val
            1155                1160                1165

Ser Ser Glu Gly Arg Phe Lys Asn Leu Arg Glu Ala Leu Lys Asn Cys
    1170                1175                1180

Asp Pro Pro Cys Val Pro Tyr Leu Gly Met Tyr Leu Thr Asp Leu Ala
1185                1190                1195                1200

Phe Ile Glu Glu Gly Thr Pro Asn Tyr Thr Glu Asp Gly Leu Val Asn
            1205                1210                1215

Phe Ser Lys Met Arg Met Ile Ser His Ile Ile Arg Glu Ile Arg Gln
            1220                1225                1230

Phe Gln Gln Thr Ala Tyr Lys Ile Glu His Gln Ala Lys Val Thr Gln
            1235                1240                1245

```
Tyr Leu Leu Asp Gln Ser Phe Val Met Asp Glu Glu Ser Leu Tyr Glu
    1250                1255                1260

Ser Ser Leu Arg Ile Glu Pro Lys Leu Pro Thr
1265                1270                1275

<210> SEQ ID NO 2
<211> LENGTH: 1262
<212> TYPE: PRT
<213> ORGANISM: Mus musculus

<400> SEQUENCE: 2

Met Gln Lys Ala Ile Arg Leu Asn Asp Gly His Val Val Thr Leu Gly
  1               5                  10                  15

Leu Leu Ala Gln Lys Asp Gly Thr Arg Lys Gly Tyr Leu Ser Lys Arg
             20                  25                  30

Ser Ala Asp Asn Pro Lys Trp Gln Thr Lys Trp Phe Ala Leu Leu Gln
         35                  40                  45

Asn Leu Leu Phe Tyr Phe Glu Ser Asp Ser Ser Pro Arg Pro Ser Gly
     50                  55                  60

Leu Tyr Leu Leu Glu Gly Ser Ile Cys Lys Arg Ala Pro Ser Pro Lys
 65                  70                  75                  80

Arg Gly Thr Ser Ser Lys Glu Ser Gly Glu Lys Gln His Tyr Phe
             85                  90                  95

Thr Val Asn Phe Ser Asn Asp Ser Gln Lys Thr Leu Glu Leu Arg Thr
        100                 105                 110

Glu Asp Ala Lys Asp Cys Asp Glu Trp Val Ala Ala Ile Ala Arg Ala
        115                 120                 125

Ser Tyr Lys Ile Leu Ala Thr Glu His Glu Ala Leu Met Gln Lys Tyr
    130                 135                 140

Leu His Leu Leu Gln Val Val Glu Thr Glu Lys Thr Val Ala Lys Gln
145                 150                 155                 160

Leu Arg Gln Gln Leu Glu Asp Gly Glu Val Glu Ile Glu Arg Leu Lys
                165                 170                 175

Thr Glu Val Thr Ile Thr Asn Leu Ile Lys Asp Asn Asp Arg Ile Gln
            180                 185                 190

Ser Ser Asn Lys Ala Gly Ser Ala Asp Glu Asp Ser Asp Ile Lys
        195                 200                 205

Lys Ile Lys Lys Val Gln Ser Phe Leu Arg Gly Trp Leu Cys Arg Arg
    210                 215                 220

Lys Trp Lys Asn Ile Ile Gln Asp Tyr Ile Arg Ser Pro His Ala Asp
225                 230                 235                 240

Ser Met Arg Lys Arg Asn Gln Val Val Phe Ser Met Leu Glu Ala Glu
                245                 250                 255

Ala Glu Tyr Val Gln Gln Leu His Ile Leu Val Asn Asn Phe Leu Arg
            260                 265                 270

Pro Leu Arg Met Ala Ala Ser Ser Lys Lys Pro Pro Ile Thr His Asp
        275                 280                 285

Asp Val Ser Ser Ile Phe Leu Asn Ser Glu Thr Ile Met Phe Leu His
    290                 295                 300

Gln Ile Phe Tyr Gln Gly Leu Lys Ala Arg Ile Ser Ser Trp Pro Thr
305                 310                 315                 320

Leu Val Leu Ala Asp Leu Phe Asp Ile Leu Leu Pro Met Leu Asn Ile
                325                 330                 335

Tyr Gln Glu Phe Val Arg Asn His Gln Tyr Ser Leu Gln Ile Leu Ala
            340                 345                 350
```

```
His Cys Lys Gln Asn Arg Asp Phe Asp Lys Leu Leu Lys Gln Tyr Glu
            355                 360                 365

Ala Lys Pro Asp Cys Glu Glu Arg Thr Leu Glu Thr Phe Leu Thr Tyr
    370                 375                 380

Pro Met Phe Gln Ile Pro Arg Tyr Ile Leu Thr Leu His Glu Leu Leu
385                 390                 395                 400

Ala His Thr Pro His Glu His Val Glu Arg Asn Ser Leu Asp Tyr Ala
                405                 410                 415

Lys Ser Lys Leu Glu Glu Leu Ser Arg Ile Met His Asp Glu Val Ser
            420                 425                 430

Glu Thr Glu Asn Ile Arg Lys Asn Leu Ala Ile Glu Arg Met Ile Thr
            435                 440                 445

Glu Gly Cys Glu Ile Leu Leu Asp Thr Ser Gln Thr Phe Val Arg Gln
            450                 455                 460

Gly Ser Leu Met Gln Met Ser Leu Ser Glu Lys Ser Lys Ser Ser Arg
465                 470                 475                 480

Gly Arg Leu Gly Ser Leu Ser Thr Lys Lys Glu Gly Glu Arg Gln Cys
                485                 490                 495

Phe Leu Phe Ser Lys His Leu Ile Ile Cys Thr Arg Gly Ser Gly Gly
            500                 505                 510

Lys Leu His Leu Thr Lys Asn Gly Val Ile Ser Leu Ile Asp Cys Thr
            515                 520                 525

Leu Leu Asp Glu Pro Glu Asn Leu Asp Asp Glu Ala Lys Gly Ala Gly
            530                 535                 540

Pro Glu Ile Glu His Leu Glu Phe Lys Ile Gly Val Glu Pro Lys Asp
545                 550                 555                 560

Ser Leu Pro Phe Thr Val Ile Leu Val Ala Ser Thr Arg Gln Glu Lys
                565                 570                 575

Ala Ala Trp Thr Ser Asp Ile Ile Gln Cys Val Asp Asn Ile Arg Cys
            580                 585                 590

Asn Gly Leu Met Met Asn Ala Phe Glu Glu Asn Ser Lys Val Thr Val
            595                 600                 605

Pro Gln Met Ile Lys Ser Asp Ala Ser Leu Tyr Cys Asp Asp Val Asp
            610                 615                 620

Ile Arg Phe Ser Lys Thr Met Asn Ser Cys Lys Val Leu Gln Ile Arg
625                 630                 635                 640

Tyr Ala Ser Val Glu Arg Leu Leu Glu Arg Leu Thr Asp Leu Arg Phe
                645                 650                 655

Leu Ser Ile Asp Phe Leu Asn Thr Phe Leu His Ser Tyr Arg Val Phe
            660                 665                 670

Thr Asn Ala Met Val Val Leu Asp Lys Leu Ile Asn Ile Tyr Arg Lys
            675                 680                 685

Pro Met Ser Ala Ile Pro Ala Arg Ser Leu Glu Leu Leu Phe Ser Ser
            690                 695                 700

Ser His Asn Ala Lys Leu Leu Tyr Gly Asp Ala Pro Lys Ser Pro Arg
705                 710                 715                 720

Ala Ser Arg Lys Phe Ser Ser Pro Pro Leu Ala Ile Gly Thr Ser
                725                 730                 735

Ser Pro Ser Arg Arg Arg Lys Leu Ser Leu Asn Ile Pro Ile Ile Thr
            740                 745                 750

Gly Gly Lys Ala Leu Glu Leu Ala Ser Leu Gly Cys Ser Ser Asp Ser
            755                 760                 765
```

```
Tyr Ala Asn Ile His Ser Pro Ile Ser Pro Phe Gly Lys Thr Thr Leu
770                 775                 780

Asp Thr Gly Lys Leu Cys Met Ala Ser Ser Leu Pro Lys Thr Pro Glu
785                 790                 795                 800

Glu Ile Asp Val Pro Ala Thr Ile Pro Glu Lys Pro Gly Glu Leu Ser
                805                 810                 815

Ala Ser Arg Lys His Ser Ser Asp Val Leu Lys Glu Ser Glu Asp
            820                 825                 830     Asp

Asp Gln Asn His Ser Asp Glu Asp Asn Thr Glu Val Ser Pro Val Lys
                835                 840                 845

Ser Pro Pro Thr Pro Lys Ser Phe Leu Asn Arg Thr Ile Thr Glu Phe
850                 855                 860

Pro Phe Phe Asn Tyr Asn Asn Gly Ile Leu Met Thr Thr Cys Arg Asp
865                 870                 875                 880

Leu Val Asp Asn Asn Arg Ser Thr Leu Ser Ala Thr Ser Ala Phe Ala
                885                 890                 895

Ile Ala Thr Ala Gly Ala Asn Glu Gly Pro Ser Asn Lys Glu Val Phe
                900                 905                 910

Arg Arg Met Ser Leu Ala Asn Thr Gly Phe Ser Ser Asp Gln Arg Asn
                915                 920                 925

Ile Asp Lys Glu Phe Val Ile Arg Arg Ala Ala Thr Asn Arg Val Leu
            930                 935                 940

Asn Val Leu Arg His Trp Val Thr Lys His Thr Gln Asp Phe Asp Thr
945                 950                 955                 960

Asp Asp Thr Leu Lys Tyr Arg Val Ile Cys Phe Leu Glu Glu Val Met
                965                 970                 975

His Asp Pro Asp Leu Leu Thr Gln Glu Arg Lys Ala Ala Ala Asn Ile
            980                 985                 990

Ile Arg Thr Leu Thr Leu Glu Glu Thr Thr Glu Gln His Ser Met Leu
        995                 1000                1005

Glu Glu Val Ile Leu Met Thr Glu Gly Val Lys Thr Glu Pro Phe Glu
    1010                1015                1020

Asn His Pro Ala Leu Glu Ile Ala Glu Gln Leu Thr Leu Leu Asp His
1025                1030                1035                1040

Leu Val Phe Lys Ser Ile Pro Tyr Glu Glu Phe Phe Gly Gln Gly Trp
                1045                1050                1055

Met Lys Ala Glu Lys Tyr Glu Arg Thr Pro Tyr Ile Met Lys Thr Thr
                1060                1065                1070

Lys His Phe Asn His Val Ser Asn Phe Ile Ala Ser Glu Ile Ile Arg
            1075                1080                1085

Asn Glu Asp Ile Ser Ala Arg Ala Ser Ala Ile Glu Lys Trp Val Ala
1090                1095                1100

Val Ala Asp Ile Cys Arg Cys Leu His Asn Tyr Asn Ala Val Leu Glu
1105                1110                1115                1120

Ile Thr Ser Ser Ile Asn Arg Ser Ala Ile Phe Arg Leu Lys Lys Thr
            1125                1130                1135

Trp Leu Lys Val Ser Lys Gln Thr Lys Ser Leu Leu Asp Lys Leu Gln
                1140                1145                1150

Lys Leu Val Ser Ser Asp Gly Arg Phe Lys Asn Leu Arg Glu Ser Leu
            1155                1160                1165

Arg Asn Cys Asp Pro Pro Cys Val Pro Tyr Leu Gly Met Tyr Leu Thr
1170                1175                1180

Asp Leu Val Phe Ile Glu Glu Gly Thr Pro Asn Tyr Thr Glu Asp Gly
```

```
1185                1190                1195                1200
Leu Val Asn Phe Ser Lys Met Arg Met Ile Ser His Ile Ile Arg Glu
                1205                1210                1215
Ile Arg Gln Phe Gln Gln Thr Thr Tyr Lys Ile Asp Pro Gln Pro Lys
                1220                1225                1230
Val Ile Gln Tyr Leu Leu Asp Glu Ser Phe Met Leu Asp Glu Glu Ser
                1235                1240                1245
Leu Tyr Glu Ser Ser Leu Leu Ile Glu Pro Lys Leu Pro Thr
                1250                1255                1260

<210> SEQ ID NO 3
<211> LENGTH: 1244
<212> TYPE: PRT
<213> ORGANISM: Rattus norvegicus

<400> SEQUENCE: 3

Met Gln Lys Ala Ile Arg Leu Asn Asp Gly His Val Val Ser Leu Gly
 1               5                   10                  15
Leu Leu Ala Gln Arg Asp Gly Thr Arg Lys Gly Tyr Leu Ser Lys Arg
                20                  25                  30
Ser Ser Asp Asn Pro Lys Trp Gln Thr Lys Trp Phe Ala Leu Leu Gln
                35                  40                  45
Asn Leu Leu Phe Tyr Phe Glu Ser Asp Ser Ser Ser Arg Pro Ser Gly
            50                  55                  60
Leu Tyr Leu Leu Glu Gly Ser Ile Cys Lys Arg Met Pro Ser Pro Lys
 65              70                  75                  80
Arg Gly Thr Ser Ser Lys Glu Ser Asp Lys Gln His His Tyr Phe Thr
                85                  90                  95
Val Asn Phe Ser Asn Asp Ser Gln Lys Ser Leu Glu Leu Arg Thr Asp
                100                 105                 110
Asp Ser Lys Asp Cys Asp Glu Trp Val Ala Ile Ala Arg Ala Ser
                115                 120                 125
Tyr Lys Ile Leu Ala Thr Glu His Glu Ala Leu Met Gln Lys Tyr Leu
            130                 135                 140
His Leu Leu Gln Val Val Glu Thr Glu Lys Thr Val Ala Lys Gln Leu
145             150                 155                 160
Arg Gln Gln Leu Glu Asp Gly Glu Val Glu Ile Glu Arg Leu Lys Ala
                165                 170                 175
Glu Ile Ala Asn Leu Ile Lys Asp Asn Glu Arg Ile Gln Ser Asn Gln
            180                 185                 190
Leu Val Ala Pro Glu Asp Glu Asp Ser Asp Ile Lys Lys Ile Lys Lys
            195                 200                 205
Val Gln Ser Phe Leu Arg Gly Trp Leu Cys Arg Arg Lys Trp Lys Asn
            210                 215                 220
Ile Ile Gln Asp Tyr Ile Arg Ser Pro His Ala Asp Ser Met Arg Lys
225             230                 235                 240
Arg Asn Gln Val Val Phe Ser Met Leu Glu Ala Glu Ala Glu Tyr Val
                245                 250                 255
Gln Gln Leu His Ile Leu Val Asn Asn Phe Leu Arg Pro Leu Arg Met
                260                 265                 270
Ala Ala Ser Ser Lys Lys Pro Pro Ile Thr His Asp Asp Val Ser Ser
            275                 280                 285
Ile Phe Leu Asn Ser Glu Thr Ile Met Phe Leu His Gln Ile Phe Tyr
            290                 295                 300
```

```
Gln Gly Leu Lys Ala Arg Ile Ala Ser Trp Pro Thr Leu Val Leu Ala
305                 310                 315                 320

Asp Leu Phe Asp Ile Leu Leu Pro Met Leu Asn Ile Tyr Gln Glu Phe
            325                 330                 335

Val Arg Asn His Gln Tyr Ser Leu Gln Ile Leu Ala His Cys Lys Gln
        340                 345                 350

Asn Arg Asp Phe Asp Lys Leu Leu Lys Gln Tyr Glu Ala Lys Pro Asp
    355                 360                 365

Cys Glu Glu Arg Thr Leu Glu Thr Phe Leu Thr Tyr Pro Met Phe Gln
370                 375                 380

Ile Pro Arg Tyr Ile Leu Thr Leu His Glu Leu Leu Ala His Thr Pro
385                 390                 395                 400

His Glu His Val Glu Arg Asn Ser Leu Asp Tyr Ala Lys Ser Lys Leu
            405                 410                 415

Glu Glu Leu Ser Arg Val Met His Asp Glu Val Ser Glu Thr Glu Asn
        420                 425                 430

Ile Arg Lys Asn Leu Ala Ile Glu Arg Met Ile Thr Glu Gly Cys Glu
    435                 440                 445

Ile Leu Leu Asp Thr Ser Gln Thr Phe Val Arg Gln Gly Ser Leu Ile
450                 455                 460

Gln Val Pro Met Ser Glu Lys Gly Lys Ile Asn Lys Gly Arg Leu Gly
465                 470                 475                 480

Ser Leu Ser Leu Lys Glu Gly Glu Arg Gln Cys Phe Leu Phe Ser
            485                 490                 495

Lys His Leu Ile Ile Cys Thr Arg Gly Ser Gly Ser Lys Leu His Leu
            500                 505                 510

Thr Lys Asn Gly Val Ile Ser Leu Ile Asp Cys Thr Leu Leu Asp Asp
    515                 520                 525

Pro Glu Asn Met Asp Asp Gly Lys Gly Gln Glu Val Asp His Leu
530                 535                 540

Asp Phe Lys Ile Trp Val Glu Pro Lys Asp Ser Pro Phe Thr Val
545                 550                 555                 560

Ile Leu Val Ala Ser Ser Arg Gln Glu Lys Ala Ala Trp Thr Ser Asp
            565                 570                 575

Ile Ile Gln Cys Val Asp Asn Ile Arg Cys Asn Gly Leu Met Met Asn
        580                 585                 590

Ala Phe Glu Glu Asn Ser Lys Val Thr Val Pro Gln Met Ile Lys Ser
    595                 600                 605

Asp Ala Ser Leu Tyr Cys Asp Asp Val Asp Ile Arg Phe Ser Lys Thr
610                 615                 620

Met Asn Ser Cys Lys Val Leu Gln Ile Arg Tyr Ala Ser Val Glu Arg
625                 630                 635                 640

Leu Leu Glu Arg Leu Thr Asp Leu Arg Phe Leu Ser Ile Asp Phe Leu
            645                 650                 655

Asn Thr Phe Leu His Ser Tyr Arg Val Phe Thr Asp Ala Val Val Val
        660                 665                 670

Leu Asp Lys Leu Ile Ser Ile Tyr Lys Lys Pro Ile Thr Ala Ile Pro
    675                 680                 685

Ala Arg Ser Leu Glu Leu Phe Ser Ser His Asn Thr Lys Leu
690                 695                 700

Leu Tyr Gly Asp Ala Pro Lys Ser Pro Arg Ala Ser Arg Lys Phe Ser
705                 710                 715                 720

Ser Pro Pro Pro Leu Ala Ile Gly Thr Ser Ser Pro Val Arg Arg Arg
```

```
                    725                 730                 735
Lys Leu Ser Leu Asn Ile Pro Ile Ile Thr Gly Gly Lys Ala Leu Glu
            740                 745                 750
Leu Ala Ser Leu Gly Cys Pro Ser Asp Gly Tyr Thr Asn Ile His Ser
            755                 760                 765
Pro Ile Ser Pro Phe Gly Lys Thr Thr Leu Asp Thr Ser Lys Leu Cys
            770                 775                 780
Val Ala Ser Ser Leu Thr Arg Thr Pro Glu Glu Ile Asp Met Thr Thr
785                 790                 795                 800
Leu Glu Glu Ser Ser Gly Phe Arg Lys Pro Thr Ser Asp Ile Leu Lys
                    805                 810                 815
Glu Glu Ser Asp Asp Gln Ser Asp Val Asp Asp Thr Glu Val Ser
                    820                 825                 830
Pro Pro Thr Pro Lys Ser Phe Arg Asn Arg Ile Thr Gln Glu Phe Pro
            835                 840                 845
Leu Phe Asn Tyr Asn Ser Gly Ile Met Met Thr Cys Arg Asp Leu Met
            850                 855                 860
Asp Ser Asn Arg Ser Pro Leu Ser Ala Thr Ser Ala Phe Ala Ile Ala
865                 870                 875                 880
Thr Ala Gly Ala Asn Glu Ser Pro Ala Asn Lys Glu Ile Tyr Arg Arg
                    885                 890                 895
Met Ser Leu Ala Asn Thr Gly Tyr Ser Ser Asp Gln Arg Asn Ile Asp
                    900                 905                 910
Lys Glu Phe Val Ile Arg Arg Ala Ala Thr Asn Arg Val Leu Asn Val
            915                 920                 925
Leu Arg His Trp Val Thr Lys His Ser Gln Asp Phe Glu Thr Asp Asp
930                 935                 940
Leu Leu Lys Tyr Lys Val Ile Cys Phe Leu Glu Val Met His Asp
945                 950                 955                 960
Pro Asp Leu Leu Pro Gln Glu Arg Lys Ala Ala Ala Asn Ile Met Arg
            965                 970                 975
Thr Leu Thr Gln Glu Glu Ile Thr Glu Asn His Ser Met Leu Asp Glu
            980                 985                 990
Leu Leu Leu Met Thr Glu Gly Val Lys Thr Glu Pro Phe Glu Asn His
            995                 1000                1005
Ser Ala Met Glu Ile Ala Glu Gln Leu Thr Leu Leu Asp His Leu Val
            1010                1015                1020
Phe Lys Ser Ile Pro Tyr Glu Glu Phe Phe Gly Gln Gly Trp Met Lys
1025                1030                1035                1040
Ala Asp Lys Asn Glu Arg Thr Pro Tyr Ile Met Lys Thr Thr Arg His
            1045                1050                1055
Phe Asn His Ile Ser Asn Leu Ile Ala Ser Glu Ile Leu Arg Asn Glu
            1060                1065                1070
Glu Val Ser Ala Arg Ala Ser Thr Ile Glu Lys Trp Val Ala Val Ala
            1075                1080                1085
Asp Ile Cys Arg Cys Leu His Asn Tyr Asn Ala Val Leu Glu Ile Thr
            1090                1095                1100
Ser Ser Ile Asn Arg Ser Ala Ile Phe Arg Leu Lys Lys Thr Trp Leu
1105                1110                1115                1120
Lys Val Ser Lys Gln Thr Lys Ser Leu Phe Asp Lys Leu Gln Lys Leu
                    1125                1130                1135
Val Ser Ser Asp Gly Arg Phe Lys Asn Leu Arg Glu Thr Leu Arg Asn
                    1140                1145                1150
```

```
Cys Asp Pro Pro Cys Val Pro Tyr Leu Gly Met Tyr Leu Thr Asp Leu
        1155            1160                1165

Ala Phe Leu Glu Glu Gly Thr Pro Asn Tyr Thr Glu Asp Gly Leu Val
    1170            1175                1180

Asn Phe Ser Lys Met Arg Met Ile Ser His Ile Ile Arg Glu Ile Arg
1185                1190                1195                1200

Gln Phe Gln Gln Thr Thr Tyr Lys Ile Glu Pro Gln Pro Lys Val Thr
            1205                1210            1215

Gln Tyr Leu Val Asp Glu Thr Phe Val Leu Asp Asp Glu Ser Leu Tyr
            1220            1225            1230

Glu Ala Ser Leu Arg Ile Glu Pro Lys Leu Pro Thr
        1235            1240
```

METHOD FOR IDENTIFYING AN ANTAGONIST OF GUANINE NUCLEOTIDE RELEASING FACTOR 1

This application is a continuation of application Ser. No. 10/344,223, filed Jul. 25, 2003, now abandoned, which is a National Stage application of International Application No. PCT/FR01/02561, filed Aug. 7, 2001, which claims the benefit of French Application No. 00-10539, filed Aug. 10, 2000.

The present invention relates to the field of biology and of cell signaling in neurons. More specifically, the present invention relates to novel uses of all or part of GRF1 (Guanine Nucleotide Releasing Factor 1) protein for screening molecules exhibiting an activity of protection against neuronal death and of treatment for obesity. GRF1 protein, which is represented diagrammatically in FIG. 1A, was originally discovered in humans for its ability to modulate the activation state of p21Ras protein. The sequences of the human, mouse and rat GRF1 proteins are, respectively, the sequences SEQ ID No. 1, SEQ ID No. 2 and SEQ ID No. 3. Application WO 93/21314 and U.S. Pat. No. 5,656,595 describe the identification, isolation and also characterization of the human form of this protein.

GRF1 has several functional domains, termed PH, IQ, DH and CDC25 domains, the meaning and involvement of which are specified hereinafter.

The location of the functional domains of GRF1 on the human, mouse and rat protein sequences is indicated in the table hereinafter.

GRF1 comprises a DH (Db1 homology) domain which exhibits strong sequence homology with a region of the proto-oncogene Db1. Db1 is an exchange factor for the small G proteins of the Rho/Rac/Cdc42Hs family involved in the regulation of various cell signals controlling either cytoskeletal motility or the activation of "stress" kinases (1).

In the Db1 protein, the activity of exchange of GDP/GTP on the proteins of the Rho family is carried by the DH domain. This domain is found in other low molecular weight G protein exchange factors, including the GRF1 proteins and the SOS proteins. Results have been published which suggest that the DH domain of GRF1 is functional on Rac (activation of Rac in GTP form) and leads to activation of JNK1 in cells in culture which overexpress the beta/gamma subunit of heterotrimeric G proteins (2). Moreover, the functional role of the DH domain of GRF1 in neuronal processes has also been suggested by the results of site-directed mutagenesis experiments which show that activation of GRF1 protein by calcium requires an intact DH domain (3, 4).

Calcium plays an important role in the regulation of neuronal activities: neuromediator secretion, neuron growth, cell death/survival, adaptation and stimulation of synaptic transmission, transcriptional activation of certain genes. Studies carried out on primary cultures of newborn rat cortex neurons have shown that activation of Ras by GRF1 is increased in the presence of calcium. This activation is regulated by the binding of calmodulin to the IQ domain of GRF1 (3-5).

As regards the exchange activity of GRF1 for the Ras proteins (Ha, Ki and N-Ras), it is carried by the region homologous to CDC25 of *Saccharomyces cerevisiae*, located at the carboxy-terminal end of the molecule (6).

GRF1 has two PH (Pleckstrin Homology) domains which are domains of interaction between proteins and which are probably involved in binding to the beta-gamma subunits of heterotrimeric G proteins (7-9).

The functions of the GRF1 protein, initially discovered for its exchange activity on the proto-oncogene Ras, are today known in greater detail. Contrary to the SOS1, SOS2 and GRF2 proteins, three other exchange factors for Ras which are expressed ubiquitously, it is now accepted that expression of the grf1 gene is restricted to the central nervous system in humans, mice and rats (6, 10, 11).

In the brain, the regionalization of this expression has been finely studied. In the rat, it is considerable in the hippocampus, the neocortex, some deep nuclei and the granule cells of the anterior lobe of the cerebellum (12). In mice, it has also been described as being abundant in the amygdala (13) and the hypothalamus (14).

Among the various cell types present in the central nervous system, expression of the grf1 gene appears to be restricted to neurons (15). This gene undergoes strict transcriptional control over time, since it is not expressed during embryonic life and only begins to be transcribed at the time of birth, to reach a maximum level around the fifteenth day (14, 15).

The expression of grf1 is controlled by a particular transcriptional mechanism called parental imprinting, which, in mice, results in expression of the gene from the allele of paternal origin, whereas the maternal allele is silent (14, 16). It is interesting to note that some genes (proto-oncogenes) normally subjected to parental imprinting are involved in cell proliferation and the appearance of tumors when there is a loss of the imprinting mechanism and the two alleles are transcribed.

Although the pathway for Ras activation by the SOS exchange factors is well documented, it appears that very little is known about the signaling pathways which use GRF1 and about its biological function in vivo.

It appears that, contrary to the Ras exchange factors of the SOS family, GRF1 does not transduce the signals resulting from the binding of ligands to receptors with tyrosine kinase activity, but rather those derived from heterotrimeric G protein-coupled receptors with seven transmembrane domains (17-19).

Finally, it will be noted that it has been possible to touch on some of the biological functions of GRF1 in vivo, by virtue of studying the phenotype of mice carrying an inactivating mutation of the grf1 gene—knockout or KO mice, obtained by the homologous recombination technique—which no longer express GRF1 (13, 14). These animals perform relatively poorly, or are even deficient, in tests of learning and memory which use "aversive" stimuli. According to the authors of this work, the integrity of the region of the brain called the amygdala is thought to be impaired in the mutant mice and responsible for the phenotype observed (13). However, no indication is given regarding a possible use of these mice for screening molecules exhibiting a therapeutic activity.

Physical damage to the brain, such as cerebral ischemia or cerebral trauma (acute or accidental damage), and neurodegenerative diseases, such as Alzheimer's disease and Parkinson's disease, remain one of the primary causes of mortality and morbidity in developed countries.

It has been shown that apoptosis constitutes one of the mechanisms leading to this damage.

A considerable number of molecules acting on various physiopathological events caused by attacks on the central nervous system have been evaluated successfully in experimental research in various models and species. Although some of them have been or are used in clinical trials for these disorders, none of the molecules tested has shown any real effectiveness during phase III studies or when they have been placed on the market. The only medication currently used to treat cerebral ischemia consists of injecting thrombolytics only in patients who do not exhibit any hemorrhagic risks.

The applicant has shown, by studying mice carrying an inactivating mutation of the grf1 gene, that the absence of expression of the GRF1 protein imparts protection against physical damage to the brain during cerebral ischemia.

Furthermore, over a few tens of years, obesity has become a major public health problem in industrial countries, where it now affects 20 to 30% of the population. These numbers should further increase alarmingly in the years to come. Because its causes are multifactorial and the sources thereof lie, to lesser or greater degrees, among environmental factors on the one hand (dietary behaviors, access to food, expending of energy, etc.) and multiple genetic origins on the other hand, obesity constitutes a true challenge for medicine.

The physiopathology of diseases linked to weight is complex and heterogeneous. Obesity is commonly associated with an increased risk of death, with cardiovascular diseases, with non-insulin-dependent diabetes and with insulin resistance. Psychological and behavioral disorders such as anxiety and depression were also added to the clinical picture of the disease. Moreover, and phenotypically at the opposite end of the spectrum, excessive weight loss in particular environmental (malnutrition) or pathological (mental anorexia for example) contexts is associated with considerable morbidity and mortality. For these various reasons, the identification of a gene which plays a role in weight gain is of considerable value whether the emphasis is on the treatment of obesity or on that of excessive weight loss.

The applicant has shown by studying mice carrying an inactivating mutation of the grf1 gene, that expression of the GRF1 protein is essential for regulation of the expression of leptin. Leptin is a cytokine associated with the feeling of satiety which plays a major role in controlling weight gain (20).

Within the scientific context as just summarized, a need still exists for better understanding of the various mechanisms involved which may lead in particular to disorders involving neuronal apoptosis or associated with leptin metabolism.

There is also a need for medicinal products which are effective in the treatment of disorders of the central nervous system and in the treatment of obesity.

The applicant set out to search for compounds intended for the prevention and/or treatment of disorders affecting in particular the central nervous system and obesity.

It has shown, using mice carrying an inactivating mutation of the grf1 gene as study model, that GRF1 is involved in these disorders.

The present invention therefore relates to the use of all or part of the GRF1 protein, or of cells expressing all or part of the GRF1 protein, in methods for detecting compounds intended for the prevention and/or treatment of pathological conditions or of disorders of the central nervous system involving neuronal death, such as apoptosis, or associated with leptin metabolism. It also relates to compounds intended for the prevention and/or treatment of pathological conditions or of disorders of the central nervous system involving neuronal death, or associated with obesity or with leptin metabolism.

The GRF1 protein is preferentially of human origin. It may, however, be of any other origin, and in particular may be mouse GRF1 protein or the GRF1 protein for any other mammal. It may also be any protein exhibiting at least 85%, and preferentially 90%, identity with a GRF1 protein, and in particular with the human GRF1 protein having the sequence SEQ ID No. 1, or with a GRF1 protein of animal origin, such as those having the sequences SEQ ID No. 2 or SEQ ID No. 3. The expression "part of the GRF1 protein" is intended to mean an amino acid sequence comprising a functional part of the GRF1 protein, and in particular the sequences corresponding to all or part of one of the PH, DH or CDC25 domains of the GRF1 proteins.

One of the advantages of the screening methods which are the subject of the present invention lies in particular in the position of GRF1 upstream of the JNKs (FIG. 1B), which has the advantage that it is possible to specifically regulate the JNK activation pathways which would involve GRF1.

Another advantage lies in the demonstration of the lack of toxicity of these compounds, the grf1-knockout mice being viable and in good health.

The screening method according to the present invention using all or part of the GRF1 protein may comprise steps consisting of measuring:

the phosphorylation of the GRF1 protein; or the exchange activity of the GRF1 protein on either proteins of the Ras family (Ha, K, N-Ras), or the Rac and Cdc42 proteins, directly or indirectly, or the interaction between the GRF1 protein and either the beta-gamma subunits of the heterotrimeric G proteins or the small G proteins of the Ras family, namely Rac and Cdc42;

cellular transformation by GRF1.

Thus, according to a first advantageous embodiment, the present invention relates to a method for screening or for detecting compounds intended for the prevention and/or treatment of pathological conditions of the central nervous system involving neuronal death or associated with leptin metabolism, comprising the steps consisting in:

(i) culturing cells expressing the GRF1 protein in the presence of a labeled phosphorylated compound and a test compound, (ii) lyzing said cells, and (iii) measuring the amount of labeled GRF1 protein.

The cell lyzate obtained in step (ii) can be incubated in microtitration plate wells precoated with an anti-GRF1 antibody.

The GRF1 phosphorylation can also be measured using an antibody specific for phosphorylated amino acid.

Thus, according to another advantageous embodiment, the present invention relates to a method for screening or for detecting compounds intended for the prevention and/or treatment of pathological conditions of the central nervous system involving neuronal death or associated with leptin metabolism, comprising the steps consisting in:

(i) culturing cells expressing the GRF1 protein in the presence of a test compound, (ii) lyzing said cells, (iii) measuring the amount of phosphorylated GRF1.

The amount of phosphorylated GRF1 is preferentially measured using an antibody specific for a phosphorylated amino acid.

Said cells can be cultured in a medium containing orthophosphate labeled with $P^{32}$ or with $P^{33}$.

The phosphorylation of the GRF1 protein can be carried out in said neuronal cells by adding carbachol to the culture medium, or else in cell lines starved of serum overnight and then re-incubated in the presence of serum, or alternatively in cell lines cotransfected with cDNAs encoding the trimeric G protein beta-gamma subunits $\beta 1\gamma 2$ or $\beta 1\gamma 5$, then starved of serum overnight and then reincubated in the presence of serum.

According to another embodiment of the invention, the screening comprises measuring the exchange activity of GRF1 on certain proteins of the small G protein family (Ras, Rac, Cdc42). Thus, according to yet another advantageous embodiment, the present invention relates to a method for screening or for detecting compounds intended for the prevention and/or treatment of pathological conditions of the central nervous system involving neuronal death or associated with leptin metabolism, comprising the steps consisting in:
(i) bringing into contact all or part of the GRF1 protein, a protein of the small G protein family loaded with labeled GDP or GTP, and a test compound,
(ii) adding respectively unlabeled GTP or GDP,
(iii) measuring the amount of labeled G protein.

Such a protein of the small G protein family may in particular be Ras (53, 54, 55), Rac (56, 57, 58) or Cdc42 (59).

The exchange activity of the GRF1 protein on proteins of the Ras family, or the Rac and CDC42 proteins, can be measured in vitro in an acellular medium by incubating, in microtitration plate wells, a reaction mixture comprising said small G proteins in the recombinant state, loaded with tritiated GDP, cold GTP, and all or part of the GRF1 protein in the recombinant state. An aliquot fraction of said reaction mixture is taken and filtered over a membrane and the radioactivity which is retained thereon is measured, or else the content of each of said wells is passed over a PD10 column and the radioactivity of the eluate is measured.

Said small G proteins in the recombinant state may be chosen from the group consisting of the wild-type Ras, Cdc42 or Rac proteins either in the form of fusion proteins and expressed in *E. coli* or in mammalian cells, or in a tagged form in a baculovirus, expressed in insect cells and purified. The amount of nucleotides exchanged can also be demonstrated by retention.

Advantageously, GST-Raf (RBD domain) or GST-PAK (CRIB domain) fusion proteins, and a mixture of anti-GST IgG and SPA (scintillation proximity assay) protein A PVT coupled to microspheres (Amersham), are added and the fluorescence of said microtitration plates is measured after centrifugation. The GDP-bound forms do not allow interaction. The sequences of PAK and Raf have been published (see respectively references 60 to 64, and 65 to 69).

The Ras (or Rac) recombinant protein is incubated with cold GDP. Ras-GDP (or Rac-GDP) forms. Tritiated GTP and GRF1 are then added. The exchange reaction takes place. Ras-tritiated GTP forms. After 60 minutes, a GST-Raf fusion protein is added (or GST-PAK if working with Rac). The fusion protein interacts with Ras-GTP, the amount of which in the medium is dependent on the exchange activity of GRF1. The microspheres, which are coupled to an anti-GST antibody, are added. The GST-Raf/Ras-tritiated GTP complex attaches to the spheres. These spheres have the ability to scintillate when they are in the proximity of a radioactive source. They then make it possible to quantify the proportion of Ras-GTP and therefore the exchange activity of GRF1 in the medium.

The screening method can also be used in a cellular system.

Thus, it may be carried out by bringing the compounds to be screened into contact with a yeast transformed with grf1 and in which the CDC25 and/or CDC24 genes have been inactivated or mutated. Advantageously, the membrane of such a yeast is permeabilized beforehand and/or at least one of the genes involved in the mechanisms of detoxification has been inactivated.

It may also be simply carried out in an *S. cerevisiae* yeast transformed with grf1. The lifting of the metabolic disorders created by the expression of grf1 is then measured.

The screening method may also be a "double-hybrid" system of protein-protein interaction comprising a first hybrid protein consisting of a protein from fusion between Ras, CDC42Hs or Rac and a DNA-interacting domain, and a second hybrid protein consisting of a protein from fusion between all or part of GRF1 and a transactivating domain. It may also be a "double-hybrid plus one" system consisting in expressing, in the nucleus of the same *S. cerevisiae* yeast, either all or part of GRF1, PAK1 (CRIB domain) fused with a transactivating domain and either Rac or CDC42Hs fused with a DNA-interacting domain, or all or part of GRF1, c-Raf1 (RBD) fused with a transactivating domain and Ras fused with a DNA-interacting domain.

Finally, the screening may be a cellular screening comprising the steps consisting in
(i) transfecting immortalized mammalian cells with a vector expressing a grf1 transgene (all or part) and imparting on said cells the transformed phenotype and resistance to a selection agent,
(ii) selecting said cells transfected and expressing the transgene and cloning them in an agar growth support, the transformation with GRF1 allowing the cells to grow without adhering,
(iii) adding said test compounds to a suspension of said cells, and
(iv) detecting said GRF1-inhibiting compounds by a decrease in the number of clones obtained on the growth medium.

According to another aspect, the present invention relates to the use of compounds, as screened by one of the detection methods mentioned above, in the preparation of medicinal products.

According to yet another aspect, the present invention relates to the use of mice carrying an inactivating mutation of the grf1 gene, as a model for studying the prevention of pathological conditions or of disorders involving neuronal death or associated with leptin metabolism.

As has already been mentioned, the subject of the present application is to search for compounds intended for the production of medicinal products for the prevention and/or treatment of various pathological conditions of the central nervous system (A) and of obesity (B). Because of the central role of GRF1, the methods which are the subject of the present application can also be used to screen molecules exhibiting activity against certain cardiovascular diseases (B), and pathological angiogenic processes (C), and with respect to other biological molecules (D).

A—Central Nervous System
1—Acute Neurodegenerative Diseases

The present invention makes it possible to screen compounds which antagonize the effect of the activity of GRF1 and which impart protection against neuronal death induced by cerebral ischemia, cranial or cerebral trauma, and spinal or medullary trauma.

2—Neuronal Death and Apoptosis

The methods which are the subject of the present invention can be used to screen molecules for the treatment or prevention of neurodegeneration involving neuronal apoptosis, of Parkinson's disease, of Alzheimer's disease, of senile dementia, of Huntington's chorea, of amyotrophic lateral sclerosis, of epilepsy, of multiple sclerosis, of cerebella and spinal cerebella disorders, of cognitive disorders, of cranial trauma, of medullary trauma, of traumas of the inner ear, of retinal traumas, of glaucomas, and of cancers of the nervous system.

3—Others

The methods which are the subject of the present invention can be used to screen molecules for the treatment or prevention of psychoses including schizophrenia, of anxious disorders, of depression, of panic attacks, of peripheral neuropathies, of migraine, of shaking, of obsessive-compulsive disorder, of thymic disorders, of tardive dyskinesia, of bipolar disorders, of drug-induced movement disorders, of dystonias, of endotoxemic shocks, of hemorrhagic shocks, of hypotension, of insomnia, of immunological diseases, of vomiting, of appetite disorders (bulimia, anorexia), of obesity, of memory disorders, in withdrawal from chronic treatment and alcohol abuse or drug abuse (opioids, barbiturates, cannabis, cocaine, amphetamine, phencyclidine, hallucinogens, benzodiazepines for example), as analgesics or potentiators of the analgesic activity of narcotic and non-narcotic medicinal products.

B—Obesity/Cardiovascular Diseases

The present invention makes it possible to search for compounds which antagonize the activity of GRF1 and which play a protective role against weight gain, mainly in adult individuals.

GRF1 is thought to be involved in the upstream regulation of leptin synthesis, directly or indirectly. Leptin is a hormone known to inhibit the release of Neuropeptide-Y (NPY), an appetite-stimulating molecule produced by the neurons of the arcuate nucleus of the hypothalamus (20, 21). It also controls the synthesis of an anorectic peptide: CART (cocaine- and amphetamine-regulated transcript) in the arcuate nucleus (22). The antagonist activities of these two neuropeptides consequently balance the effect of the leptin signal on food intake. Leptin also stimulates the alpha-MSH/melanocortin 4-receptor anorectic circuit (23-25).

GRF1 is liable to contribute to the signal in pathways which use the neuromediators (which bind to receptors with seven transmembrane domains). The absence thereof in our mutant mice might result in a signal of the "satiety and/or increase in the expending of energy" type with, consequently, a decrease in fat mass and a low leptinemia.

C—Angiogenesis

The vascular endothelium appears to be a new target for leptin. Recent results show that leptin stimulates endothelial cell proliferation and angiogenesis in vivo (26, 27).

Angiogenesis plays an important role in embryogenesis, cicatrization and the menstrual cycle, but also in pathological situations such as tumor vascularization, rheumatoid arthritis, psoriasis, Kaposi's sarcoma, diabetic retinopathies and atherosclerosis.

The present inventors have shown that adult mice knockout for the grf1 gene have a leptin content much lower than that of control animals. It is possible that the mutant animals exhibit a certain form of protection against the appearance of pathological angiogenic processes and, consequently, against the growth and dissemination of tumors and against all the above-mentioned pathological conditions.

GRF1 antagonists which would lead to a decrease in leptinemia might have a protective role against these diseases. A contraceptive role can also be envisioned.

D—Other Biological Targets

Leptin is involved in triggering puberty and controlling reproduction (28-32).

Leptin also plays a role in regulating the T-lymphocyte-regulated immune response (33).

Modulators of GRF1 activity might have an effect on the immune function and on mechanisms of reproduction. The latter hypothesis appears, moreover, to be verified, since the observations of the present inventors indicate delayed puberty and early menopause in the grf1 KO mouse. This phenomenon may be due in part to the decrease in leptin level or to deregulation of synthesis of sex hormones controlled by the hypothalamo-hypophyseal axis.

The inhibitory properties of the leptin with respect to bone synthesis have recently been demonstrated. It acts by inhibiting the activity of osteoblasts, a population of cells responsible for bone formation (34). Modifying leptinemia by acting on GRF1 might make it possible to treat diseases associated with a decrease in bone density, such as, for example, osteoporosis, or conversely those associated with considerable calcification, such as for example osteopetrosis.

Studies carried out on mice knockout for the NPY gene have shown that these animals exhibit a pronounced taste for alcohol and are more resistant to its sedative and hypnotic effects than wild-type mice (35). Leptin plays a negative role on NPY release (20, 21). Modulators of GRF1 activity might be used in the treatment of alcoholic behavior and in the treatment of sleep disorders.

Figure 1B:
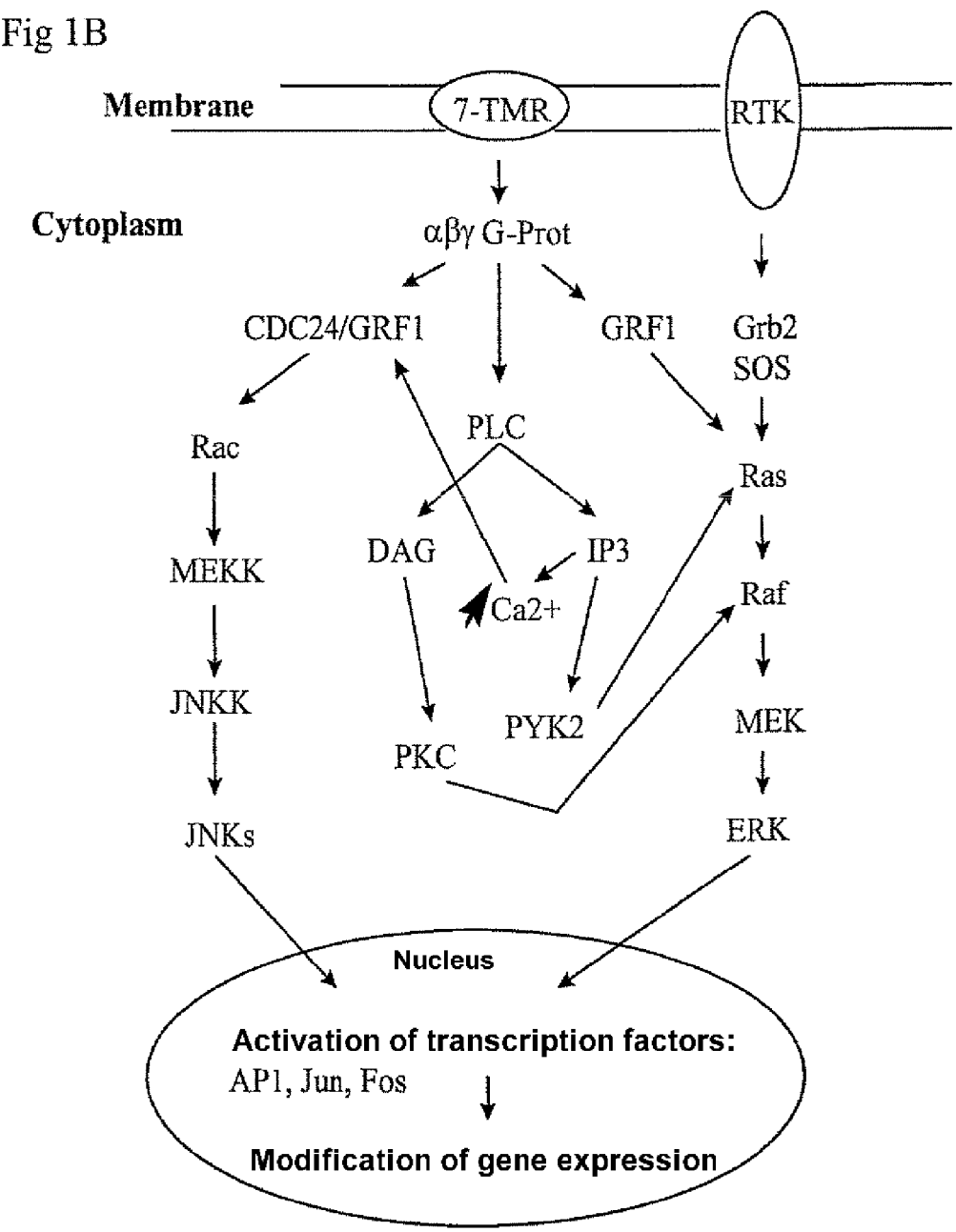
Figure 2A:
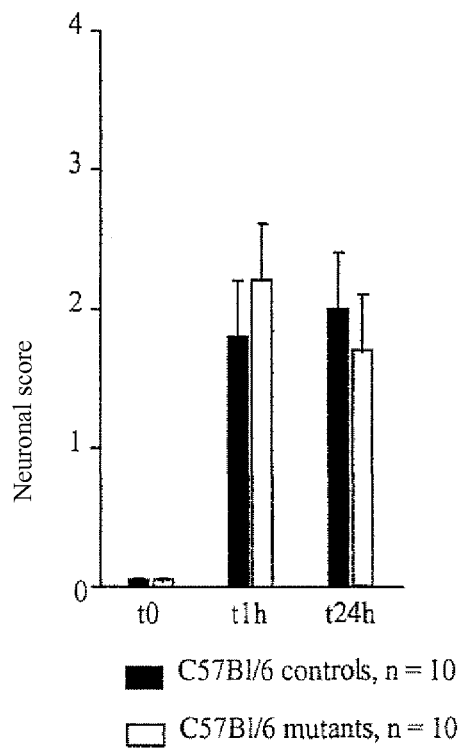
Figure 2B:
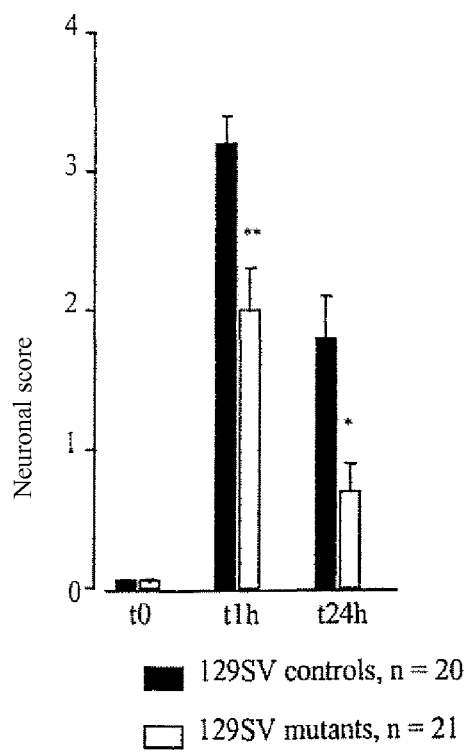
Figure 3A:
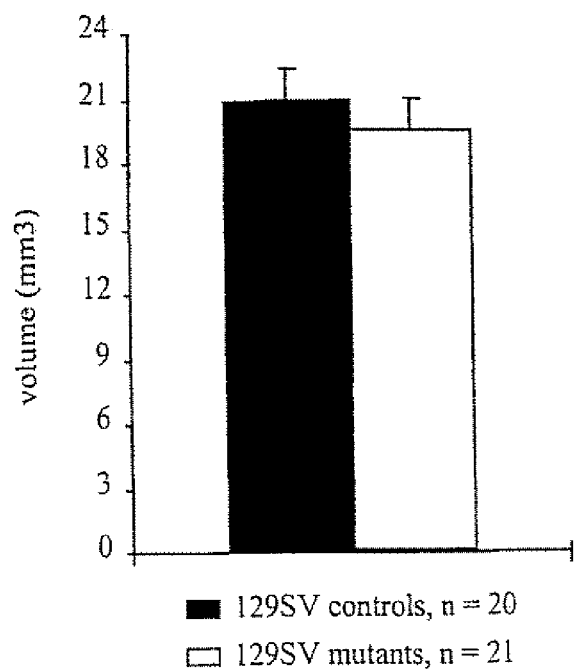
Figure 3B:
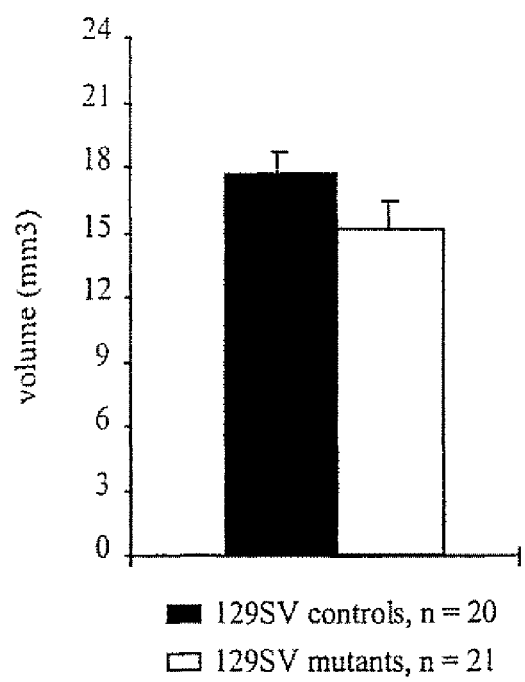
Figure 3C:
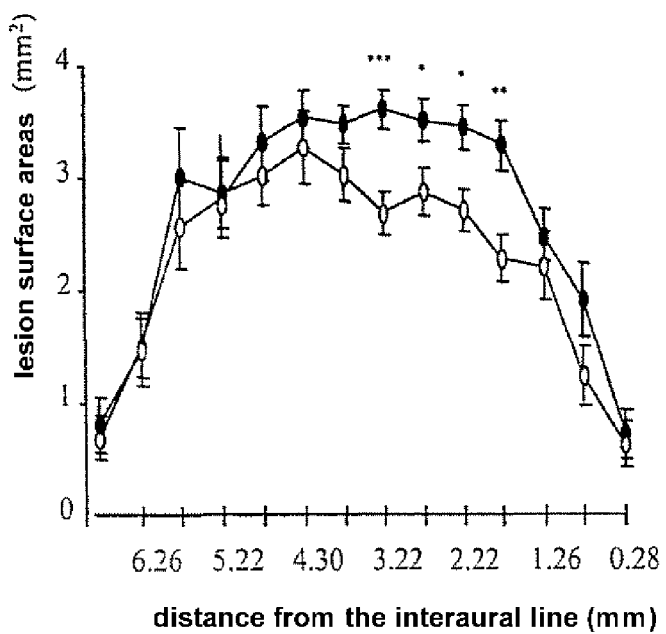
Figure 3D:
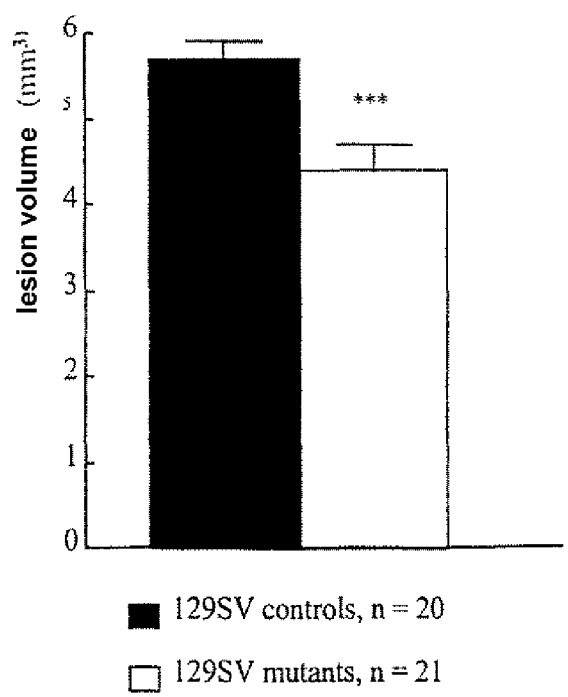

Other additional subjects, characteristics and advantages will be described below with reference to the examples of preparation which follow, given purely by way of nonlimiting illustration, and with reference to the attached drawings in which:

FIG. 1A is a diagrammatic representation of GRF1 protein,

FIG. 1B is a diagram combining the main signaling pathways which involve GRF1 protein function FIGS. 2A and 2B are histograms representing neurological examinations, FIGS. 3A and 3B are histograms illustrating the extent of the brain lesions respectively overall and of the cortex, FIG. 3C illustrates the lesions of the various areas of the cortical region, FIG. 3D illustrates the volume of the lesions of the cortical region between 3.22 and 1.76.

Figure 4A:
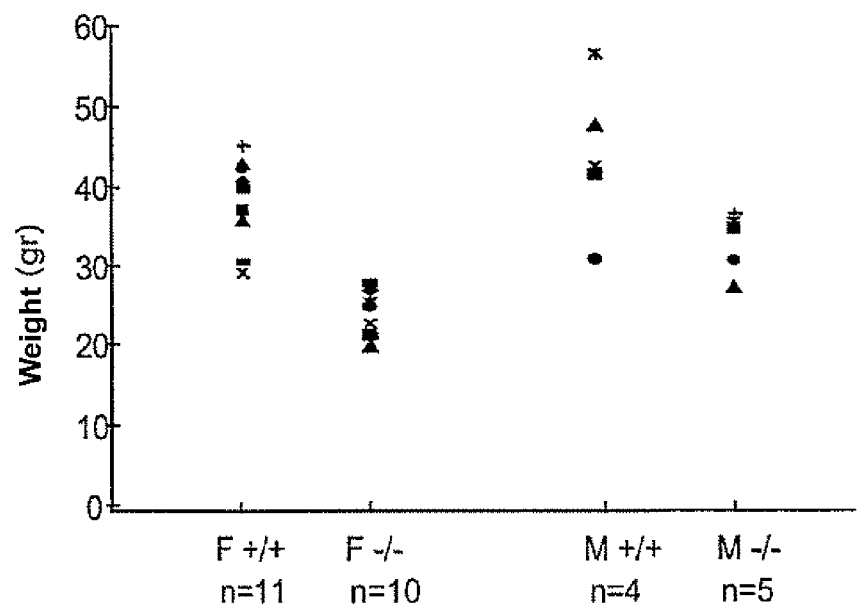
Figure 4B:
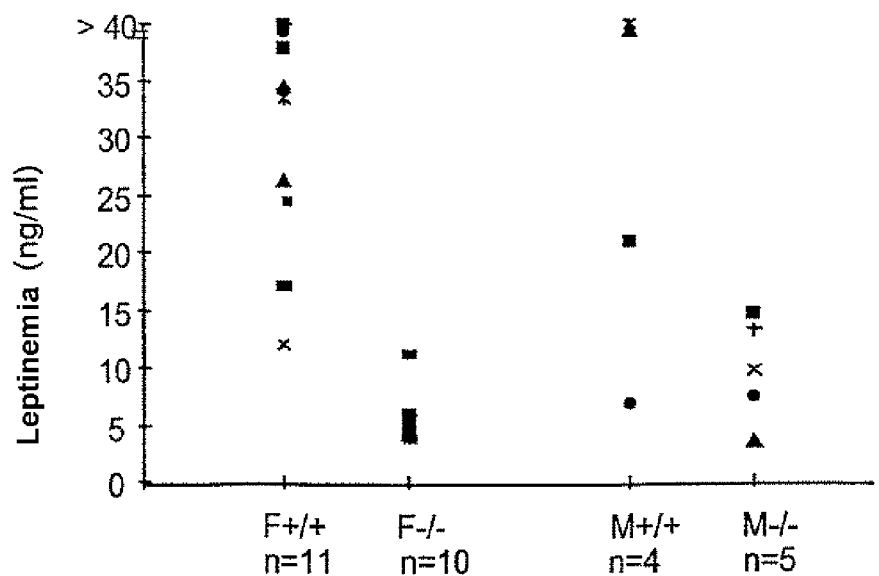
Figure 5A:
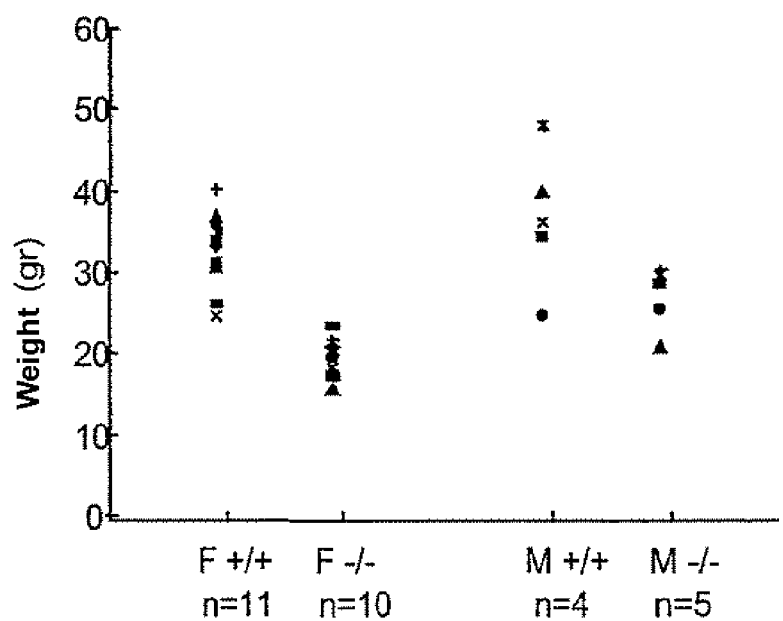
Figure 5B:
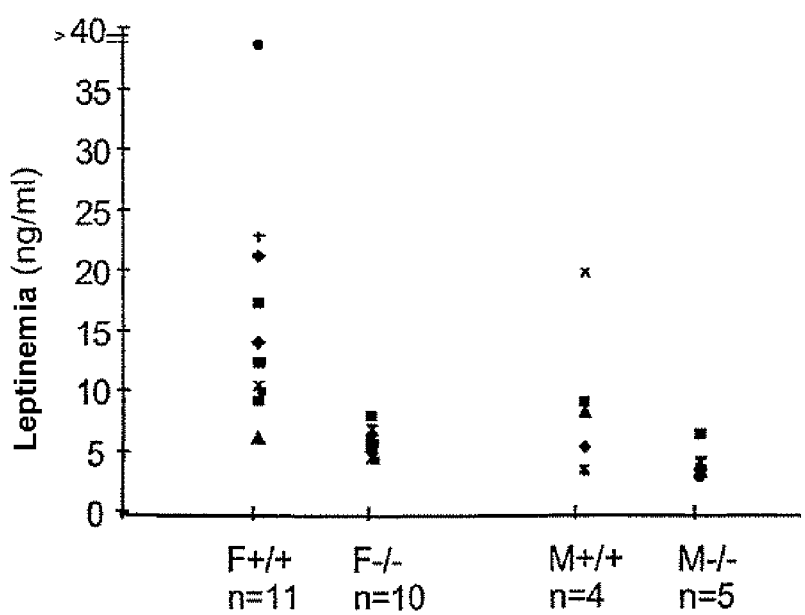

FIGS. 4A and 4B illustrate, respectively, the weight and the leptinemia of grf1 KO mutant mice (noted −/−) and wild-type mice (noted +/+), and FIGS. 5A and 5B illustrate, respectively, the weight and the leptinemia of grf1 KO mutant mice and wild-type mice after fasting for 48 h.

EXAMPLES

Example 1

Use of Mice Carrying an Inactivating Mutation of the grf1 Gene ("grf1 Knockout" or "grf1 KO" Mice) as a Model for Studying Protection Against Neuronal Death Induced by Cerebral Ischemia The grf1 KO mice offer the possibility of investigating the impact of the GRF1 protein-dependent pathways on cerebral ischemia. KO mice and wild-type mice are subjected to a permanent focal cerebral ischemia. The parameters measured in order to determine the bearing of GRF1 on the ischemic damage result (i) from an examination of neurological function and (ii) from a histological quantification of the brain lesions.

1.1.: Model for Permanent Focal Cerebral Ischemia

Male mice weighing 22-37 g, derived from the C57Bl/6 and 129SV genetic backgrounds, anesthetized with halothane at 1.4% in a nitrous oxide-oxygen mixture (70:30), are used. An incision is made between the eye and the left ear. The temporal muscle is folded back. A craniotomy is performed at the level of the temporal bone, which allows access to the middle cerebral artery. This is cauterized by electrocoagulation. A permanent focal cerebral ischemia is then caused by a left middle cerebral artery occlusion (MCA.O, (36)). During surgery, both the temperature of the temporal muscle and the body temperature are maintained at normal levels. The incision is then sutured, and the animals are put back in their cages in a room heated at 24-26° C.

The mice are divided into groups as follows:

Mice deficient for GRF1 expression (KO mice): mutants C57Bl/6 (n=10), mutants 129 SV (n=21).

The wild-type mice used as controls are control C57Bl/6 (n=10) and control 129 SV (n=20).

1.2.: Neurological Examination

For the neurological examination, the following procedure is carried out:

Before ischemia, and then 1 h and 24 h after ischemia, a neurological examination, initially described in rats (37) and slightly modified by the present inventors, is performed. During the examination, various points are scored: 0 (normal), 1 (flexing of the front leg), 2 (circular movement), 3 (flexing of the front leg and twisting of the thorax), 4 (loss of righting reflex).

As can be noted on FIGS. 2A and 2B, all the mice reveal a significant neurological deficiency, in comparison to their own pre-ischemia neuronal score, 1 h and 24 h post-MCA.O. In the C57Bl/6 mice, no difference is observed between the wild-type mice and the KO mice in all of the points examined at the time. However, compared to the wild-type mice, the 129SV-KO mice exhibit a clearly less pronounced deficiency 1 h ($p<0.01$) and 24 h ($p<0.05$) post-ischemia.

1.3: Brain Lesion

The following procedure is carried out: after having had their "neuroscore" noted, the mice are sacrificed and the brains are rapidly removed and frozen in liquid isopentane at −30° C. Coronal sections 40 μm thick are cut at various stereotaxic levels with a cryostat, and are then stained with 0.5% cresyl violet. The areas of lesion are measured with an image analyzer (Leica Q500) at various coronal levels. The volume of the brain lesions is then calculated by integration of the surface areas.

In the C57Bl/6 mice, no significant difference is observed between the wild-type mice and the KO mice (results not shown). As can be noted in FIGS. 3A and 3B, in the 129SV mice, no significant overall or cortical decrease in the brain lesion is observed.

However, significant decreases in areas of lesion are noted at certain stereotaxic levels (FIG. 3C), this result corresponding to a 23% decrease ($p<0.05$) in the lesion in this specific region (FIG. 3D).

The results described in example 1 above show that the absence of the grf1 gene results in better functional recovery in the 129SV-KO mice in which ischemia was induced.

The decrease in the lesions in specific coronal levels might correspond to the structures involved in the motor and sensory-motor functions examined (in particular the neocortex and the cerebellum), in which the grf1 gene might be highly expressed (12). However, no effect is noted in the mice with a C57Bl/6 genetic background.

Inactivation of the grf1 gene might interrupt one of the signaling pathways leading to apoptosis. In other words, the results reported above suggest that the GRF1 protein contributes to the signaling which leads to neuronal apoptosis by intervening in the pathway of stress kinase activation or activation of one or more of the small G proteins of the Rho, Rac and Cdc42 protein family. GRF1 activity has, moreover, been described on the Rac protein (2).

In summary, the GRF1 protein might activate, in part, an apoptotic pathway responsible for vulnerability to ischemia. These results also suggest that the GRF1 protein itself might represent a target in particular for acute neurodegenerative disorders.

Example 2

Use of Mice Carrying an Inactivating Mutation of the grf1 Gene ("grf1 Knockout" or "grf1 KO" Mice) as a Model for Studying Protection Against Obesity 2.1: Obesity 10-12-month-old wild-type mice, fed since weaning with a diet intended for breeding, rich in proteins (22%) and in fat (7%) (ref: D03, code: R0310. Supplier: UAR, France), has a considerable fat mass between the skin and the abdominal muscle tunic, and also in the abdominal cavity, mainly around the uterine horns in females and in the peritoneum. The presence of fat around the heart is also found in the fattest individuals which can be described as obese, and their weight of which exceeds 35 grams in females and 40 grams in males.

Under the same conditions of breeding and nutrition, the mice carrying the inactivating mutation for the grf1 gene, a year or more old, show no characteristics describing obesity. The majority of them have no adipose tissue between the skin and the abdominal wall. In females, the deposit of fat around the uterine horns is very small and comparable in amount to that of 6-8-week-old wild-type animals. The adult grf1 KO mice are also characterized by a lack of fat in the peritoneum and around the heart.

It is observed that inactivation of the grf1 gene in adult mice results in protection against weight gain and the accumulation of adipose tissue.

2.2: Leptinemia

In order to correlate the observations made in the grf1 KO mice and wild-type mice with known characteristics of the obese phenotype, the assayed plasma leptin in the wild-type and mutant mice.

Leptin is a cytokine whose effect is to decrease food intake and to increase the expending of energy. The relationship of proportionality exists between, firstly, the number of adipocytes—which secrete leptin—and the size of the lipid vesicles which they contain and, secondly the plasma concentration of this hormone (20).

The present inventors have determined the weight and the leptinemia of one-year-old male and female wild-type mice or mice mutant (KO) for the grf1 gene. The group of animals studied consists of several sibships. Each sibship is composed of wild-type and mutant animals.

The blood samples were taken at the time of euthanasia of the animals by decapitation.

The plasma leptin was assayed using a radioimmunoassay (RIA) manufactured by the company Linco, in the form of a kit (ref: ML-82K) which is marketed in France by the company Cliniciences.

As can be observed in FIGS. 4A and 4B, in the mutant mice (noted −/−), the plasma leptin content is very low compared to that of the control wild-type mice of the same age (noted +/+). This reference is made to the literature, the leptinemia of the grf1 knockout mice more than 12 months old is comparable to that of very young mice of 6-8 weeks (5 to 10 ng/ml). Comparative examination of the outline for these animals completely agrees with this.

If the animals are made to fast for 48 h (FIGS. 5A and 5B), there ensues a decrease in body weight accompanied, in the control animals, by a considerable decrease in the plasma leptin concentration, whereas, in the KO animals, the decrease in leptinemia is very small. The latter result suggests that, in the KO animals, the leptin content is already at a minimum threshold which can only be slightly modulated in response to prolonged fasting.

The first measurements of food consumption in the mutant mice indicate that food intake is decreased compared to the controls. However, if the amount of food absorbed is related back to the weight of the animals, there is no significant difference between the KOs and the wild-types.

It should be noted that, while the cause of the phenotype of the mutant mice is an increase in the expending of energy, the latter does not appear to be due to hyperactivity of the grf1 KO mice.

Example 3

Use of the GRF1 Protein for Screening Compounds by Measuring Serine/Threonine or Tyrosine Phosphorylation of the GRF1 Protein This experiment is carried out on cells in culture.

GRF1 phosphorylation is induced in the cells in culture in various ways.

Three protocols are used:
1) Radioactive Labeling and Immunoprecipitation of the GRF1 Protein These various treatments are carried out in the presence and absence of the molecules to be screened, in culture medium containing orthophosphate labeled with $P^{32}$ or with $P^{33}$ (200 µCi at 1 mCi/10 mm Petri dish). The cells are lyzed under cold conditions in an HNTG buffer (20 mM hepes, pH 7.5, 150 mM NaCl, 0.1% Triton, 10% glycerol, in the presence of inhibitors of the proteases and the phosphatases: 1 mM $Na_3VO_4$, 2.2 µg/ml aprotinin, 1 µg/ml leupeptin, 1 µg/ml antipain, 10 µg/ml benzamidine, 1 µg/ml soybean trypsin inhibitor, 1 µg/ml chymostatin, 1 µg/ml pepstatin-A) or RIPA buffer (50 mM Tris, pH 8.0, 150 mM NaCl, 1% NP-40, 0.5% sodium deoxycholate, 0.1% SDS, 1 mM $Na_3VO_4$, 100 µM phenylmethylsulfonylfluoride (PMSF), 25 µg/ml aprotinin, 25 µg/ml leupeptin). The GRF1 protein is then immunoprecipitated using an anti-GRF1 antibody or anti-tag antibody (10) (epitope recognized by monoclonal antibody and allowing detection or immunoprecipitation of the tagged protein, such as FLAG, myc or hemagglutinin (HA)), and the immunoprecipitate is then separated on an SDS-4-20% polyacrylamide gel. The radioactivity of the band corresponding to the GRF1 protein (140 kDa) is quantified using a radiation detector of the PhosphorImager type.

The effectiveness of a molecule is calculated by the percentage inhibition of phosphorylation of the GRF1 protein, considering the value found for the nonstimulated cells to be the value 0% and the value found for the cells stimulated in the absence of the screened molecule to be the value 100%.
2) Radioactive Labeling and Retention of the GRF1 Protein in CYTOSTAR Plates The first alternative to this method consists in incubating the cell lyzate previously obtained, in wells of CYTOSTAR plates (marketed by the company Amersham) precoated with an anti-GRF1 or anti-tag antibody in order to retain the GRF1 protein therein. After rinsing, quantification of the radioactive signal is obtained using a scintillation counter.
3) Quantification by ELISA A second alternative to this method consists in treating the cells as above, but in the absence of labeled orthophosphate. The cell lyzates are then used according to the ELISA assaying method. For this assay, the wells of the plates are coated with an anti-GRF1 or anti-tag antibody and the GRF1 phosphorylation is revealed and quantified with a second antibody which may or may not be labeled (radioelement, fluorescence, enzyme, etc.), and which may be either an anti-phosphotyrosine or an anti-phosphoserine/phosphothreonine. When the second antibody is not labeled, the revelation and quantification are carried out using a third anti-species antibody directed against the second and labeled. After rinsing, the signal is quantified using the radioactivity counter or a fluorescence spectrophotometer, or by measuring an enzyme activity, which leads to reading of optical density by spectrophotometry (plate readers).

The cells in culture may be:
primary cultures of neuronal cells, maintained in culture for 10 days in order to allow expression of the endogenous GRF1 protein;
cell lines in culture, of any tissue origin, transfected with a vector allowing expression of the GRF1 protein (murine or human), whole and possibly tagged. Any plasmid or viral vector which allows expression of heterologous cDNAs in mammalian cells may be used.

The phosphorylation of the GRF1 protein in the cells in culture is obtained in the neuronal cells by adding 100 µM of carbachol (5 to 30 minutes) to the culture medium of the neurons.

For the nonneuronal cells transfected with the cDNA encoding GRF1, the phosphorylation of the protein of interest is studied under the following conditions:
either the transfected cells are depleted of serum overnight, and then incubated in the presence of 10% fetal calf serum,
or the cells are cotransfected with the cDNAs encoding the trimeric G protein beta-gamma subunits β1γ2 or β1γ5. The expression vectors are plasmids which allow expression in eukaryotic cells under the control of promoters of the CMV or SV40 type (examples, pSV2 or else pcDNA3 (INVITROGEN)). The cDNAs encoding the proteins of interest are inserted therein after amplification of the fragments of PCR, verification of this sequence and subcloning of the fragments into the multiple cloning sites present in the vectors. The cells are deprived of serum overnight, and then reincubated in the presence of serum.

Example 4

Use of the GRF1 Protein for Screening Compounds by Measuring the Exchange Activity on the Ras Protein or the Rac or Cdc42 Proteins in the Presence of GRF1

These activities can be measured in acellular systems (use of recombinant proteins) or in cellular systems.
1) Measuring in Acellular Systems The recombinant Ras, Rac or Cdc42 proteins, at the final concentration of 0.5 µM, are incubated in the presence of $^3$H-GDP (0.5 µM final concentration, NEN, 111 µmol, 9 Ci/mmol) in the exchange buffer (50 mM Tris-HCl, pH 7.5, 1 mM $MgCl_2$, 10 mM dithiothreitol, 1 mM EDTA, 1 mg/ml bovine serum albumin) for 30 minutes at 30° C., and then kept in ice. $MgCl_2$ is then added to have a final concentration of 10 mM, in order to block the exchange reaction, and then 50 µl of each incubation are removed (Ras/Rac/Cdc42 bound to tritiated GDP) and are distributed in one of the 96 wells of a microplate.

The exchange reaction is started by addition to the wells of 10 µl of 10 mM cold GTP (0.1 mM final concentration), of recombinant GRF1 protein (all or parts) and of the test molecules.

After incubation for 60 minutes at 30° C., a 40 µl aliquot is removed and filtered through a 0.45 µm nitrocellulose membrane (96-well plate with bottoms covered with a filtration membrane able to retain the proteins, sartorius SM 11306). The radioactivity (tritiated GDP bound to small protein G) is counted in a scintillation counter, in the presence of scintillation fluid. In this case, it is the radioactivity which is then retained on the nylon filtration membrane which is counted.

An alternative to the filtration reaction consists in passing the contents of each well, after incubation, over a PD10 column preequilibrated with elution buffer (50 mM Tris-HCl, pH 7.5, 5 mM $MgCl_2$, 1 mM PMSF, 5 mM DTT and 1 mM EDTA). In this case, it is the radioactivity of the eluate from the column which is measured (4 ml of elution buffer passed over the column+10 ml of Beckman ReadyGel scintillation fluid).

In both cases, the exchange activity is measured by the difference in amount of radioactivity in the presence of GRF1 protein compared to that obtained in an assay without GRF1 protein. The effectiveness of a molecule is calculated by the inhibition of this exchange activity.

The recombinant Ras, Rac or Cdc42 proteins may be wild-type Ras, Cdc42 or Rac proteins of various origins (human, murine, etc.) expressed:

either in the form of fusion proteins (GST, pGEX-1λt or -2T system, Pharmacia product) in *E. coli* (according to the protocol described by the manufacturer and after transformation of the plasmids in BL21 bacteria. Protein expression is induced for 4 hours with a 0.5 mM IPTG (isopropyl-1-thio-beta-D-galactoside) at 30° C.) or in mammalian cells (pB-CGST (38)) in CHO cells transfected with the plasmids. The expression is obtained at 37° C. in an incubator with 5% $CO_2$ overnight. The proteins are purified on a glutathione affinity column according to the protocols supplied by Pharmacia (Biotech (GST-Gene Fusion system). These fusion proteins may or may not be cleaved by digestion with thrombin in order to delete their GST domain;

or in a tagged form (pBlueBacHis2, Invitrogen product) in baculoviruses, expressed in insect cells (Sf9, Sf21, High Five, etc.) after infection of the cells with a recombinant baculovirus obtained according to the methods recommended by the seller. Expression is carried out at 27° C. over two to four days and the proteins are then purified on a nickel column.

The recombinant GRF1 proteins may be whole or fractions of GRF1 proteins of various origins (human, murine, etc.) containing the exchange domains, either CDC25 or DH, or both, expressed in baculoviruses or in *E. coli*, and purified on an affinity column.

A variant of the preceding technique consists in using the ability either of Ras-GTP to bind to Raf-1 via the Ras-Binding domain (RBD) of Raf, or of Rac1-GTP or Cdc42-GTP to bind to PAK1 via the CRIB domain of the latter (39). The SPA (Scintillation Proximity Assay) system, described in U.S. Pat. No. 4,568,649, EP 154 734 and JP 84/52452, makes it possible to demonstrate and quantify the binding between two proteins in a high throughput screen.

The recombinant Ras, CDC42 or Rac proteins—in this experiment, the small Gs will be cleaved from their GST domain or else expressed with another tag, for example H is tail, etc.,—at the final concentration of 0.5 µM, are incubated in the presence of cold GDP in the exchange buffer (50 mM Tris-HCl, pH 7.5, 1 mM $MgCl_2$, 10 mM dithiothreitol, 1 mM EDTA, 1 mg/ml bovine serum albumin) for 30 minutes at 30° C., and then kept in ice. The subsequent steps consist in adding $MgCl_2$ to a final concentration of 10 mM in order to block the exchange reaction, and then in removing 50 µl of each incubation and distributing them in one of the 96 wells on a microplate.

The exchange reaction is started by addition to the wells of 10 µl of tritiated GTP (NEN 111 µmol, 9 Ci/mmol), of the recombinant GRF1 protein and of the test molecules.

After incubation for 60 minutes at 30° C., 80 µl of GST-Raf (RBD domain) or GST-PAK (CRIB domain) proteins at the concentration of 0.0013 mg/ml in a 50 mM Tris-HCl buffer, pH 7.5, containing 2 mM dithiothreitol, and 40 µl of a mixture of anti-GST immunoglobulin (0.12 mg/ml) and SPA protein A PVT coupled to microspheres (Amersham; 12.6 mg/ml) in a 50 mM Tris-HCl buffer, pH 7.5, containing 2 mM dithiothreitol and 2 mM $MgCl_2$, are added. The plates are then sealed, agitated for 1 h at 22° C., and then centrifuged at 760 g for 2 minutes and counted in a scintillation counter.

The effectiveness of the molecule is calculated by the percentage inhibition of the exchange activity and is equal to: 100×(1−(value in the presence of GRF1 and of the molecule−control in the absence of GRF1 and of the molecule)/(value in the presence of GRF1 and in the absence of the molecule−control in the absence of GRF1 and of the molecule)).

2) Measuring in Cellular Systems (Yeast)

Various possibilities can be envisioned. They use either yeast (*Saccharomyces cerevisiae*) complementation systems, or competition systems producing a physiological disorder, or the double-hybrid system. All the techniques and methods which use yeast are widely described in the literature (40-45).

The use of one or other of these systems can be envisioned due to the existence in the yeast of low molecular weight protein G/exchange factor couples, homologous to those described in mammalian cells. As regards the G proteins, the yeast RAS proteins are homologous to the mammalian Ras proteins (the latter complement the inactivating mutations of RAS proteins in yeast) and the S.c. CDC42 protein is homologous to the mammalian Rac proteins. As regards the exchange factors, CDC25 and SDC25 are homologous to GRF1 and their catalytic portions are active on the mammalian Ras proteins (46, 47). GRF1, by virtue of its domain homologous to CDC25, is capable of complementing any inactivating mutation of CDC25, or else of a double mutant CDC25/SDC25 (the SDC25 mutants or KOs having no phenotype). An exchange factor, called CDC24, which can be complemented by the DH domain of Vav is also known for S.c. CDC42 (48). It is possible to extrapolate an exchange activity for all or part (including the DH domain) of GRF1 on CDC42 in a yeast mutant for CDC24, these inactivating mutations having a lethal phenotype.

This activity of GRF1 (all or part) would totally or partially (depending on its affinity) mimic the effect of CDC24.

2.1 Complementation in Yeast

In this system, GRF1 (all or part) is capable of mimicking the function of the yeast exchange factors (CDC25, CDC24) when they are inactivated by a mutation leading to a phenotype of the growth arrest type. The effect of this complementation is to allow survival of the yeast by restoring growth. A molecule which inhibits the function of GRF1 (whole protein, CDC25 domain, DH domain) on the RAS or CDC42 proteins, in an inactivated CDC25 or CDC24 context (thermosensitive mutations), leads to loss of the complementation phenomenon and to the death of the cell at permissive temperature. The specificity of the method of action of the molecule on the RAS/CDC25 or CDC42 domain/DH domain system will be verified by measuring the action of the molecule on a wild-type yeast (information regarding the antifungal activity).

The screening will be carried out, for small molecules, in a yeast permeabilized by techniques known to those skilled in the art, consisting in raising the intracellular concentration of the molecules by adjusting the membrane permeability and the expression of genes involved in detoxification processes (for example using mutants of the Erg6 gene and/or of the genes of the PDR family). These "permeabilization" techniques are described in the following patent applications: FR 9411509 and WO 96/1082.

Yeast Strains Used

A strain of the genus *S. cerevisiae*, CDC25 TS or CDC24 TS (thermosensitive mutations), is used. It can only grow under permissive temperature conditions. It is grown on the following culture medium:

Minimum YNB medium:
yeast nitrogen base (without amino acids) (6.7 g/l) (Difco)
glucose (20 g/l) (Merck)

This medium can be solidified by adding 20 g/l of agar (Difco).

In order to allow the growth of auxotrophic yeasts on this medium, it is necessary to add thereto the nitrogenous bases or amino acids on which they are dependant, at 50 mg/ml. 100 μg/ml of ampicillin are added to the medium in order to avoid bacterial contamination.

Plasmid Construction and Amplification

The *Escherichia coli* strain TG1, having the genotype supE, hsdΔ5, thi, Δ(lac-proAB), F'[traD36 pro A$^+$B$^+$lacI$^q$lac-ZΔM15], is used to construct plasmids and to amplify and isolate plasmids. It is grown on the following medium:

LB medium:
NaCL (5 g/l) (Sigma)
bactotryptone (10 g/l) (Difco)
yeast extract (5 g/l) (Difco)

This medium can be solidified by adding 20 g/l of agar (Difco).

Ampicillin at 100 μg/ml is used to select the bacteria which have received the plasmids carrying as a marker the gene for resistance to this antibiotic.

Preparations of small amounts and of large amounts of plasmid DNA are carried out according to the protocols recommended by the manufacturer Quiagen of the DNA purification kits:

Quiaprep Spin Miniprep kit, ref: 27106
Quiaprep Plasmid Maxiprep kit, ref: 12163.

Transformation of the Yeast with a Plasmid

The yeast are made competent by treatment with LiAC/PEG according to the method described by Gietz et al. (49) and transformed with 1 μg of plasmid allowing constitutive or inducible expression of all or part of GRF1 in yeast. After the transformation steps, the yeasts are put back in culture under nonpermissive conditions. The clones selected will be those which have been complemented by GRF1.

Screening of the Molecules

A selected clone complemented by GRF1 is plated out on dishes containing the selection medium onto which drops of chemical compounds are applied. The dishes are placed under permissive conditions. The products giving a ring of yeast growth inhibition are selected and tested on a control wild-type yeast in order to eliminate the molecules with antifungal activity which give the same type of growth inhibition.

2.2 Competition with Yeast GEFs (Two Variants)

a—Constitutive Activation/Dominant Positive Effect:

In this system, the expression of all or part of GRF1 in the yeast is accompanied by a growth disturbance due to the constitutive stimulation of the exchange on the RAS or CDC42 proteins. A molecule which is active on the system will lead to a more or less complete standardization of the physiological disorder (phenotype) engendered by the expression of GRF1.

Strains Used

A wild-type yeast strain of the genus *S. cerevisiae* is used. It is grown on the minimum YNB medium as described in 2.1. The construction and the amplification of the plasmids are carried out as described in 2.1.

In the example described below, the expression of GRF1 leads to the overactivation of yeast RAS. Such yeasts will then no longer be capable of producing glycogen stores when they reach the prestationary growth phase. They will be identified by the absence of brown coloration after exposure to iodine vapor.

Screening of the Molecules

The screening will be carried out in a permeabilized yeast according to the techniques described above.

Drops of chemical compounds are applied directly to the surface of culture dishes seeded beforehand with the yeast expressing all or part of GRF1. The dishes are left to grow and then exposed to iodine vapor in a closed chamber containing iodine crystals. The products which allow yeast growth and which restore the appearance of the brown coloration will be selected as positive.

b—Constitutive Inhibitions/Dominant Negative Effect:

It is also possible to envision the expression of all or part of GRF1 behaving in the yeast as a dominant negative, inhibiting the activity of the CDC25 or CDC24 yeast proteins and causing a physiological disorder of the growth arrest type, which will be completely or partially lifted by molecules which are active on the system.

Strains Used

A wild-type strain of the genus *S. cerevisiae* is used. It is grown on the minimum YNB medium as described in 2.1. The construction and the amplification of the plasmids are carried out as described in 2.1.

Transformation of the Yeast with a Plasmid

The wild-type yeast is made competent by treatment with LiAC/PEG according to the method described by Gietz et al. (49) and transformed with 1 μg of plasmid allowing inducible expression of all or part of GRF1 in yeast (example: the expression of the grf1 gene is placed under the control of the Gal 4 gene promoter which is inducible in the presence of galactose as sole carbon source in the culture medium).

In the example described below and under induction conditions, the expression of GRF1 leads to a disturbance in the cell signaling which uses the RAS proteins in the yeast, and results in a phenotype of the growth arrest type.

Screening of the Molecules

The screening will be carried out in a permeabilized yeast according to the techniques described above.

Drops of chemical compounds are applied directly to the surface of culture dishes seeded with a yeast transformed with the plasmid for inducible expression of GRF1, but cultured beforehand in the absence of inducing agent. The dishes are incubated under conditions which allow GRF1 expression. The products which allow growth of the yeast will be selected as positive.

It is possible to envision producing these competition systems in yeast mutant (thermosensitive mutants) for RAS (RAS mut TS) complemented with a mammalian Ras, or CDC42 mut TS complemented with mammalian Rac.

2.3—Double-Hybrid and Reverse Double-Hybrid Systems/Protein-Protein Interaction

1st Application:

The use of this system makes it possible to carry out screening on molecules which can inhibit the physical interaction between Ras or Rac/CDC42Hs and GRF1 (50, 2).

The technique is based on the preparation of a first fusion protein between Ras, CDC42Hs or Rac and a DNA-interacting domain, and of a second fusion protein between GRF1 (all or CDC25-like or DH domains) and a transactivating domain. Interaction between the two hybrid proteins leads to activation of a reporter gene (HIS3, LEU2, URA3, CYH2, CAN1, LacZ, GFP, etc.). The system is used in the appropriate yeast (example: mutant ura3 if the reporter gene is URA3).

Example of a reverse double-hybrid system for screening molecules (51):

The CL9 yeast strain is used as a tool for screening molecules which interfere in the double-hybrid system. It makes it possible to demonstrate protein-protein interaction. It can be made permeable by introducing mutations in the family of PDR genes and of the ERG6 gene involved in detoxification processes.

It is grown on the minimum YNB medium.

The *Escherichia coli* strain TG1, having the genotype supE, hsdΔ5, thi, Δ(lac-proAB), F'[traD36 pro A$^+$B$^+$lacI$^q$lac-ZΔM15], is used to construct plasmids and to amplify and isolate plasmids.

The plasmids used are as follows:

The vector pGAD10, supplied by Clontech® allows expression in yeast of a fusion protein between all or part of GRF1, and the transactivating domain of GAL4 (GRF1-TA protein).

The vector pGBT9, provided by Clontech®, allows expression in yeast of a fusion protein between Ras, Rac or Cdc42 and the DNA-interacting domain of GAL4 (Ras-BD or Rac-BD or Cdc42-BD proteins).

Comment: advantageously, the carboxy-terminal domain for farnesylation of Ras or for geranylgeranylation of the Rac and Cdc42 proteins are removed from the construct. This makes it possible to obtain proteins which do not attach to the lipid membranes and which enter the cell nucleus efficiently.

Transformation of the Yeast with a Plasmid

The CL9 yeast is made competent by treatment with LiAC/PEG according to the method described by Gietz et al. (49). It is then transformed with 1 µg of each of the plasmids allowing expression of the fusion proteins, which make up the double-hybrid system. Expression of these fusion proteins leads to the strain being sensitive to cycloheximide.

A product which interferes with the interaction between the fusion proteins of the double-hybrid system will allow yeast growth on this type of medium. To carry out a screening, the yeast is plated out on the surface of a selective medium containing 10 µg/ml of cycloheximide. Drops of chemical compounds are applied directly to the surface of the dish. The products selected are those which give a halo of growth around the deposit.

The screening will be carried out in a permeabilized yeast according to the techniques described above.

In another system, inhibition of the protein-protein interaction by active molecules can be revealed by the decrease in expression of a reporter gene. This can be demonstrated, as appropriate, using a colorimetric, fluorimetric or enzyme (example: β-galactosidase) assay. Growth inhibition can be measured using a selective medium (for example: fluorate medium for the use of the URA3 reporter gene or canavanin medium for CAN1).

β-Galactosidase activity is measured in the following way:

The L40 strain of the genus *S. cerevisiae* (Mata, his3D200, trp1-901, leu2-3,112, ade2, LYS2:: (lexAop)4-HIS3, URA3:: lexAop)8-LacZ, GAL4, GAL80) is used as a screening tool. This strain makes it possible to demonstrate protein-protein interaction when one of the protein partners is fused to the LexA protein (70). It was grown on the minimum YNB culture medium.

The *Escherichia coli* strain TG1, having the genotype supE, hsdD5, thi, D(lac-proAB), F'[traD36 pro A$^+$B$^+$lacI$^q$lac-ZDM15], was used to construct plasmids and to amplify and isolate plasmids (as described in 2.1).

The plasmids used are as follows:

The vector pGAD10, provided by Clontech®, allows expression in yeast of fusion proteins between all or part of GRF1, and the transactivating domain of GAL4.

The vector pLex9 (pBTM116) allows expression in yeast of fusion proteins between Ras, Rac or Cdc42 and the DNA-interacting domain of the LexA protein.

The yeast is made competent by treatment with LiAC/PEG according to the method described by Gietz et al. (49). It is then transformed with 1 µg of each of the plasmids allowing expression of the fusion proteins, which make up the double-hybrid system. Expression of these proteins leads to expression of β-galactosidase.

A sheet of nitrocellulose is placed over the Petri dish containing the layer of yeast and the drops of chemical compounds to be screened. This sheet is then immersed in liquid nitrogen for 30 seconds in order to rupture the yeast and to thus release the β-galactosidase activity. After thawing, the sheet of nitrocellulose is placed, colonies facing upwards, in another Petri dish containing a Whatman paper presoaked with 1.5 ml of PBS solution (60 mM Na$_2$HPO$_4$, 40 mM NaH$_2$PO$_4$, 10 mM KCl, 1 mM MgSO$_4$, pH7) containing 15 µl of X-Gal (5-bromo-4-chloro-3-indoyl-β-D-galactoside) at 40 mg/ml in N,N-dimethylformamide. The dish is then placed in an incubator at 37° C. The test is described as positive when the colonies turn blue on the membrane after 6 hours.

It should be noted that, in the case of weak or very fleeting interactions between proteins, it is possible to envision introducing mutations into these proteins in order to make the interaction stronger (52).

Second Application:

This application uses the properties of interaction of PAK1 (CRIB domain) with Rac and Cdc42 when these small G proteins are in GTP-bound form, and of c-Raf1 (RBD domain) with Ras-GTP. It is then possible to envision a variant of the double-hybrid system, called double-hybrid plus one, which would consist in expression, in the nucleus of the same yeast, either:

GRF1 (all or part), PAK1 (CRIB domain) fused with a transactivating domain of GAL4 and either Rac or Cdc42 Hs fused with a DNA-interacting domain of GAL4, or GRF1 (all or part), c-Raf1 (RBD) fused with a transactivating domain GAL4 and Ras fused with a DNA-interacting domain of GAL4.

The carboxy-terminal domain for farnesylation of Ras or for geranylgeranylation of the Rac and Cdc42 proteins can be removed from the construct, which makes it possible to obtain proteins which do not attach to the lipid membranes and which enter the cell nucleus efficiently.

Activation of small Gs by GRF1 would induce their loading with GTP and therefore their interaction with their effector (PAK1 or Raf-1), and would therefore allow expression of the reporter gene as described above.

Inhibition of the exchange activity of the GRF1 protein by small molecules would therefore result in inhibition of the expression of the reporter gene (see above).

The CL9 yeast strain is used as a tool for screening molecules which interfere in the double-hybrid system. It makes it possible to demonstrate protein-protein interactions. It can be made permeable by introducing mutations in the family of PDR genes and of the ERG6 gene involved in detoxification processes. It was grown on the minimum YNB medium.

The *Escherichia coli* strain TG1, having the genotype supE, hsdΔ5, thi, Δ(lac-proAB), F'[traD36 pro A⁺B⁺lacI^q lac-ZΔM15], is used to construct plasmids and to amplify and isolate plasmids. It is grown on LB medium.

The plasmids used are as follows:

The vector pGAD10, supplied by Clontech®, allows expression in yeast of a fusion protein between PAK1 (CRIB domain) or c-Raf1 (RBD domain) and the transactivating domain of GAL4 (Pak1-TA or c-Raf1-TA protein).

The vector pGBT9, supplied by Clontech®, allows expression in yeast of a fusion protein between Ras, Rac or Cdc42 and the DNA-interacting domain of GAL4 (Ras-BD or Rac-BD or Cdc42-BD proteins).

A vector which allows expression in yeast of GRF1 (all or parts).

Transformation of the Yeast with a Plasmid

The CL9 yeast is made competent by treatment with LiAC/PEG according to the method described by Gietz et al. (49). It is then transformed with 1 μg of each of the plasmids allowing expression of the fusion proteins and GRF1, which make up the double-hybrid plus one system. Expression of these proteins leads to the strain being sensitive to cycloheximide.

A product which interferes with the activation by GRF1 of the Ras-BD, Rac-BD or Cdc42-BD fusion proteins of the system will allow yeast growth on this type of medium. To carry out a screening, the yeast is plated out over the surface of a selected medium containing 10 μg/ml of cycloheximide. Drops of chemical compounds are applied directly to the surface of the dish. The products selected are those which give a halo of growth around the deposit.

The screening is carried out in the yeast permeabilized according to the techniques described above.

The specificity of the products for the activation by GRF1 of the Ras-BD or Rac-BD or Cdc42-BD proteins will be validated using one of the other tests given as an example.

Other double-hybrid plus one system revelation techniques can be used.

By inhibiting the protein-protein interaction, the active molecules can be revealed by the decrease in expression of the reporter gene. This decrease can be demonstrated, as appropriate, using a colorimetric, fluorimetric or enzyme assay. Growth inhibition can be measured using a selective medium (for example: fluorate medium for the use of the URA3 reporter gene or canavanin medium for CAN1).

It should be noted that, in the case of weak or very fleeting interactions between proteins, it is possible to envision introducing mutations into these proteins in order to make the interaction stronger (52). In order to implement the latter examples, those skilled in the art can refer to U.S. Pat. No. 5,283,173, U.S. Pat. No. 5,468,614, U.S. Pat. No. 5,525,490, U.S. Pat. No. 5,580,736 and U.S. Pat. No. 5,885,779.

Example 5

Use of the GRF1 Protein for Screening Compounds by Measuring the Interaction Between GRF1 And the Beta-Gamma Subunits of Heterotrimeric G Proteins A physical interaction exists between the PH domain of GRF1 and the beta-gamma subunits of the hetero-trimeric G proteins (7-9). The double-hybrid system in yeast (as described in Example 4) appears to be the appropriate tool for carrying out a screen to reveal molecules capable of disturbing this interaction. It might use either the whole GRF1 protein, or the PH domains, or the series of PH-DH-PH domains as found naturally in the GRF1 protein.

Example 6

Use of GRF1 in a Cell Screening Assay for GRF1 Inhibitors, Using Transfected Cells According to the literature, overexpression of the catalytic portions of GRF1 imparts on the transfected cell the transformed phenotype (46, 47).

The screening assay for GRF1 inhibitors uses stable clones of cells transfected with grf1, for which the present inventors have been able to show overexpression of the transgene by western blotting.

Overexpression of GRF1 imparts on the cells the ability to be cloned in agar, which is verified according to the following protocol:

The cells are counted and resuspended in complete medium without phenol red, at a concentration of $2.5 \times 10^5$ cells per ml. The following are successively poured into the wells of 96-well plates:

75 μl of bottom layer containing 50% of 2× culture medium without phenol red and 50% of agarose ((1.2% low melting point agarose such as, for example, SIGMA (A-6560) type VII prepared in water and autoclaved)), 75 μl of top layer prepared from the following mixture:
  25 ml of 1.67× medium without phenol red (500 ml of 2× medium without phenol red, 100 ml of fetal calf serum, 2× glutamine and 2× penicillin/streptomycin, 100 ml of sterile water), 10 ml of cell suspension, 15 ml of agarose (1.2% low melting point agarose such as, for example, SIGMA (A-6560) type VII prepared in water and autoclaved).

Once the agar has solidified, the test molecules are diluted in 1× medium at suitable concentrations, and 75 μl are added to the layers of agar in the wells. The cells are counted after two weeks by staining with calcein:

Calcein AM (molecular probes C-1430, 4 mM DMSO) is diluted to 10 μM in HBSS and stored at −20° C. 25 μl of calcein AM are added to each well and the cells are left in the incubator (37° C.) for at least one hour. The plate is read in a C0 device.

A GRF1 inhibitor will be revealed by the decrease in the number of clones in agar. Any immortalized mammalian cell transfected with a eukaryotic expression vector (plasmid) allowing expression of all or part (CDC25-like domain or DH domain) of human or murine grf1 can also be used. This expression vector at the same time imparts the phenotype resistant to a selection agent such as hygromycin, neomycin, zeocin or the like, and as such makes it possible to select and then clone (by FACS or by limiting dilution) the cells transfected and expressing the transgene.

TABLE

Location of the functional domains of the mammalian GRF1 proteins

| Species | Human | Mouse | Rat |
|---|---|---|---|
| Protein size | 1275 | 1262 | 1244 |
| Pleckstrin homology #1 (PH) | 22-129 | 22-130 | 22-129 |
| Db1 homology (DH) domain for exchange on Rac | 244-455 | 248-459 | 244-455 |
| Pleckstrin homology #2 (PH) | 456-590 | 460-588 | 456-582 |

TABLE-continued

Location of the functional domains of the mammalian GRF1 proteins

| Species | Human | Mouse | Rat |
|---|---|---|---|
| CDC25 homology domain domain for exchange on Ras | 1045-1272 | 1032-1259 | 1014-1241 |

REFERENCES

1—Hall, A., Rho GTPases and the actin cytoskeleton. Science, 279, 509-14 (1998).
2—Kiyono, M., et al., G protein βγ subunit-dependent Rac-guanine nucleotide exchange activity of Ras-GRF1/CDC25Mm. Proc. Natl. Sci. USA, 96, 4826-4831 (1999).
3—Farnsworth, C. L., et al., Calcium activation of Ras mediated by neuronal exchange factor Ras-GRF. Nature, 376, 524-527 (1995).
4—Freshney, N W., et al., Activation of the exchange factor Ras-GRF by calcium requires an intact Dbl homology domain. FEBS Lett, 407, 111-5 (1997).
5—Buchsbaum, R., et al., The N-terminal pleckstrin, coiled-coil, and IQ domains of the exchange factor Ras-GRF act cooperatively to facilitate activation by calcium. Mol Cell Biol, 16, 4888-96 (1996).
6—Schweighoffer, F., et al., Identification of a human guanine nucleotide-releasing factor (H-GRF55) specific for Ras proteins. Oncogene, 8, 1447-1485 (1993).
7—Sawai, T., et al., Interaction between Pleckstrin homology domains and G protein betagamma-subunits: analyses of kinetic parameters by a biosensor-based method. Biol Pharm Bull. 22, 229-33 (1999).
8—Shaw, G., The pleckstrin homology domain: an intriguing multifunctional protein module. Bioessays, 18, 35-46 (1996).
9—Touhara, K., et al., Binding of G protein beta gamma-subunits to pleckstrin homology domains. J Biol Chem, 269 10217-20 (1994).
10—Martegani, E., et al., Cloning by functional complementation of a mouse cDNA encoding a homologue of CDC25, a Saccharomyces cerevisiae RAS activator. EMBO J, 11, 2151-2157 (1992).
11—Shou, C., et al., Molecular cloning of cDNAs encoding a guanine-nucleotide-releasing factor for Ras p21. Nature, 358, 351-354 (1992).
12—Wei, W., et al., Localization of the cellular expression pattern of $CDC25^{NEF}$ and ras in the juvenile rat brain. Molecular brain research, 19, 339-344 (1993).
13—Brambilla, R., et al., A role for the Ras signalling pathway in synaptic transmission and long-term memory. Nature, 390, 281-286 (1997).
14—Itier, J M., et al., Imprinted gene in postnatal role. Nature, 393, 125-126 (1998).
15—Zippel, R., et al., Ras-GRF, the activator of Ras, is expressed preferentially in mature neurons of the central nervous system. Molecular brain research, 48, 140-144 (1997).
16—Plass, C., et al., Identification of GRF1 on mouse chromosome 9 as an imprinted gene by RLGS-M. Nature genetics, 14, 106-109 (1996).
17—Shou, C., et al., Differential response of the Ras exchange factor, Ras-GRF to tyrosine kinase and G protein mediated signals. Oncogene, 10, 1887-1893 (1995).
18—Mattingly, R R. and Macara, I G., Phosphorylation-dependent activation of the Ras-GRF/$CDC25^{Mm}$ exchange factor by muscarinic receptors and G-protein βγ subunits. Nature, 382, 268-272 (1996).
19—Zippel, R., et al., The brain specific Ras exchange factor $CDC25^{Mm}$:modulation of its activity through Gi-protein-mediated signals. Oncogene, 12, 2697-2703 (1996).
20—Friedman, J M., Halaas, J L., Leptin and the regulation of body weight in mammals. Nature, 395, 763-70 (1998).
21—Schwartz, M W., et al., Identification of targets of leptin action in rat hypothalamus. J Clin Invest, 98, 1101-6 (1996).
22—Kristensen, P., et al., Hypothalmic CART in a new anorectic peptide regulated by leptin. Nature, 393, 72-6 (1998).
23—Krude, H., et al., Sever early-onset obesity, adrenal insufficiency and red hair pigmentation caused by POMC mutations in humans. Nat Genet, 19, 155-7 (1998).
24—Yeo, G S., et al., A frameshift mutation in MC4R associated with dominantly inherited human obesity. Nat Genet, 20, 111-2 (1998).
25—Vaisse, C., et al., A frameshift mutation in human MC4R is associated with a dominant form of obesity. Nat Genet, 20, 113-4 (1998).
26—Sierra-Honigmann, M R., et al., Biological action of leptin as an angiogenic factor. Science, 281, 1683-6 (1998).
27—Bouloumie, A., et al., Leptin, the product of Ob gene, promotes angiogenesis. Circ Res, 83, 1059-66 (1998).
28—Chehab, F F., et al., Correction of the sterility defect in homozygous obese female mice by treatment with the human recombinant leptin. Nat Genet, 12, 318-20 (1996).
29—Barash, I A., et al., Leptin in a metabolic signal to the reproductive system. Endocrinology, 137, 3144-7 (1996).
30—Chehab, F F., et al., Early onset of reproductive function in normal female mice treated with leptin. Science, 275, 88-90 (1997).
31—Strobel, A., et al., A leptin missense mutation associated with hypogonadism and morbid obesity. Nat Genet, 18, 213-5 (1998).
32—Clement, K., et al., A mutation in the human leptin receptor gene causes obesity and pituitary dysfunction. Nature, 392, 398-401 (1998).
33—Lord, G M., et al., Leptin modulates the T-cell immune response and reverses starvation-induced immunosuppression. Nature, 394, 897-901 (1998).
34—Ducy P. et al., Leptin inhibits bone formation through a hypothalamic relay: a central control of bone mass. Cell, 100, 197-207, 2000.
35—Thiele, T E., et al., Ethanol consumption and resistance are inversely related to neuropeptide Y levels. Nature, 396, 366-9 (1998).
36—Tamura, A., et al., Focal cerebral ischemia in the rat: 1. Description of technique and early neuropathological consequences following middle cerebral artery occlusion. J Cereb Blood Flow Metab, 1, 53-60 (1981).
37—Bederson, J A., et al., Rat middle cerebral artery occlusion: evaluation of the model and development of a neurologic examination. Stroke, 17, 472-476 (1986).
38—Chatton, B., et al., Eukaryotic GST fusion vector for the study of protein-protein associations in vivo: application to interaction of ATFa with Jun and Fos. Biotechniques, 18, 142-5 (1995).
39—Lowe, N., et al., Delineation of the Cdc42/Rac-binding Domain of p21-Activated Kinase. Biochemistry, 37, 7885-7891, (1998).
40—Methods Enzymol., Guide to yeast genetics and molecular biology, 194, 1-863 (1991).

41—Biotechnology, Yeast genetics engineering, 13, 1-354 (1989).

42—Methods in molecular biology, Yeast protocols, 53, 1-433 (1996).

43—Molecular Genetics of Yeast: A Practical Approach. Edited by John R. Johnston, 1-300 (1994).

44—The Yeast Two-Hybrid System. Paul L. Bartel and Stanley Fields, 1-356 (1997).

45—Methods in Yeast Genetics: A Laboratory Course Manual (1997).

46—Chevallier-Multon M C et al., *Saccharomyces cerevisiae* CDC25 (1038-1589) is a guanine nucleotide releasing factor for mammalian Ras proteins and is oncogenic in NIH3T3 cells. J. Biol. chem. 268, pp 11113-11119, 1993.

47—Barlat I et al., The *Saccharomyces cerevisiae* gene product SDC25 C-domain functions as an oncoprotein in NIH3T3 cells. Oncogene, 8, 215-218, 1993.

48—Han, J., et al., Lck regulates Vav activation of members of the Rho family of GTPases. Mol Cell Biol, 17, pp 1346-1353, 1997.

49—Gietz, R. D., R. H. Schiestl, A. R. Willems, and R. A. Woods. Studies on the transformation of intact yeast cells by LiAc/SS-DNA/PEG procedure. *Yeast,* 11: 355-360. 1995.

50—Mosteller, R D., et al., Analysis of interaction between Ras and CDC25 guanine nucleotide exchange factor using yeast GAL4 two-hybrid system. Methods Enzymol. 255, 135-48 (1995).

51—Leanna, C. A., Hannink M. The reverse two-hybrid system: a genetic scheme for selection against specific protein/protein interactions. *Nucleic. Acids. Research.* 96, 3341-3347. 1996.

52—Kamada, S., et al., A cloning method for caspase substrates that uses the yeast two-hybrid system: cloning of the antiapoptotic gene gelsolin. Proc Natl Acad Sci USA, 95, 8532-7 (1998).

53—Capon, D. J., Chen, E. Y., Levinson, A. D., Seeburg, P. H., and Goeddel, D. V. Complete nucleotide sequences of the T24 human bladder carcinoma oncogene and its normal homologue, Nature 302 (5903), 33-37 (1983).

54—McGrath, J. P., Capon. D. J., Smith, D. H., Chen, E. Y., Seeburg, P. H., Goeddel, D. V. and Levinson, A. D. Structure and organization of the human Ki-ras proto-oncogene and a related processed pseudogene. Nature 304 (5926), 501-506 (1983).

55—Taparowsky, E., Shimizu, K., Goldfarb, M. and Wigler, M. Structure and activation of the human N-ras gene. Cell 34 (2), 581-586 (1983).

56—Didsbury, J., Weber, R. F., Bokoch, G. M., Evans, T. and Snyderman, R. rac, a novel ras-related family of proteins that are botulinum toxin substrates, J. Biol. Chem. 264(28), 16378-16382 (1989).

57—Polakis, P. G., Weber, R. F., Nevins, B., Didsbury, J. R., Evans, T. And Snyderman, R., Identification of the ral and racl gene products, low molecular mass GTP-binding proteins from human platelets. J. Biol. Chem. 264(28), 16383-16389 (1989).

58—Drivas, G. T., Shih, A., Coutavas, E., Rush, M. G. and D'Eustachio, P. Characterization of four novel ras-like genes expressed in a human teratocarcinoma cell line. Mol. Cell. Biol. 10(4), 1793-1798 (1990).

59—Shinjo, K., Koland, J, G., Hart, M. J., Narasimhan, V., Johnson, D. I., Evans, T. and Cerione, R. A. Molecular cloning of the gene for the human placental GTP-binding protein Gp (G25K): identification of this GTP-binding protein as the human homolog of the yeast cell-division-cycle protein CDC42. Proc. Natl. Acad. Sci. U.S.A. 87(24), 9853-9857 (1990).

60—Brown, J. L., Stowers, L., Baer, M., Trejo, J., Coughlin, S, and Chant, J. Human Step 20 homologue hPAK1 links GTPases to the JNK MAP kinase pathway. Curr. Biol. 6(5), 598-605 (1996).

61—Bekri S, Adelaide J, Merscher S, Grosgeorge J, Caroli-Bosc F, Perucca-Lostanlen D, Kelley P M, Pebusque M J, Theillet C, Birnbaum D and Gaudray P. Detailed map of a region commonly amplified at 11q13→q14 in human breast carcinoma Cytogenet. Cell Genet. 79(1-2), 125-131 (1997).

62—Sanders, L. C., Matsumura, F., Bokoch, G. M. and de Lanerolle, P. Inhibition of myosin light chain kinase by p21-activated kinase. Science 283(5410), 2083-2085 (1999).

63—Sells, M. A., Boyd, J. T. and Chernoff, J. p21-activated kinase 1 (Pak1) regulates cell motility in mammalian fibroblasts. J. Cell Biol. 145(4), 837-849 (1999).

64—Bagrodia, S, and Cerione, R. A. Pak to the future. Trends Cell Biol. 9 (9), 350-355 (1999).

65—Bonner, T. I., Opperman, H., Seebury, P., Kerby, S. B., Gunnell, M. A., Young, A. C. and Rapp, U. R. The complete coding sequence of the human raf oncogene and the corresponding structure of the c-raf-1 gene Nucleic Acids Res. 14(2), 1009-1015 (1986).

66—Nassar, N., Horn, G., Herrmann, C., Scherer, A., McCormick, F., and Wittinghofer, A. The 2.2 A crystal structure of the Ras-binding domain of the serine/threonine kinase c-Raf1 in complex with RaplA and a GTP analogue Nature 375 (6532), 554-560 (1995).

67—Nassar, N., Horn, G., Herrmann, C., Block, C., Janknecht, R. and Wittinghofer, A. Ras/Rap effector specificity determined by charge reversal Nat. Struct. Bio. 3(8), 723-729 (1996).

68—Emerson, S. D., Madison, V. S., Palermo, R. E., Waugh, D. S., Scheffler, J. E., Tsao, K. L., Kiefer, S. E., Liu, S. P. and Fry, D. C. Solution structure of the Ras-binding domain of c-Raf-1 and identification of its Ras interaction surface Biochemistry 34 (21), 6911-6918 (1995).

69—Mott, H. R., Carpenter, J. W., Zhong, S., Chosh, S., Bell, R. M. and Campbell, S, L. The solution structure of the Raf-1 cysteine-rich domain: a novel ras and phospholipid binding site Proc. Natl. Acad. Sci. U.S.A. 93(16), 8312-8317 (1996).

70—Vojtek, A. B., S. M. Hollenberg, and J. A. Cooper. Mammalian Ras interacts directly with the serine/threonine kinase Raf. Cell, 74: 205-214. (1993).

The invention claimed is:

1. A method for identifying an antagonist of Guanine Nucleotide Releasing Factor 1 (GRF1), the method comprising:
   a) administering a test compound to a mouse model, wherein the mouse model is a leptin deficient mouse model or the mouse model is a cerebral ischemia mouse mode; and
   b) measuring a decrease in an amount of phosphorylated GRF1 protein in the presence of a test compound as compared to an amount of phosphorylated GRF1 protein in the absence of the test compound,
   thereby identifying the test compound as an antagonist of GRF1, wherein said antagonist is suitable for inhibiting weight gain in a subject if the test compound reduces fat deposit in the leptin deficient mouse model or neuronal death during cerebral ischemia in a subject if the test compound reduces neuronal death in the cerebral ischemia mouse model.

2. The method of claim 1, wherein the phosphorylated GRF1 protein is measured using an antibody.

3. The method of claim 1, wherein the contacting step further comprises a labeled phosphorylated compound.

4. The method of claim 1, wherein said antagonist is suitable for inhibiting weight gain.

5. The method of claim 1, wherein said antagonist is suitable for inhibiting neuronal death during cerebral ischemia.

6. The method of claim 1, wherein the GRF1 protein is expressed on a cell.

7. The method of claim 6, wherein the method further comprises the step of lysing the cell prior to the measuring step.

8. The method of claim 7, wherein the cell lysate is incubated in a well pre-coated with an anti-GRF1 antibody.

9. The method of claim 6, wherein the cell is cultured in a medium containing orthophosphate that is labeled with $P^{32}$ or $P^{33}$.

10. The method of claim 9, wherein carbachol is added to the medium.

11. The method of claim 9, wherein the cell is starved of serum overnight and then re-incubated in the presence of serum.

12. The method of claim 9, wherein the cell is co-transfected with cDNAs encoding the trimeric G protein beta-gamma subunits β1γ2 or β1γ5, then starved of serum overnight, and then reincubated in the presence of serum.

* * * * *